United States Patent
Galeotti

(12) 
(10) Patent No.: US 6,361,969 B1
(45) Date of Patent: Mar. 26, 2002

(54) EXPRESSION OF HETEROLOGOUS PROTEINS

(75) Inventor: Cesira Galeotti, Siena (IT)

(73) Assignee: Chiron S.p.A., Siena (IT)

( * ) Notice: Subject to any disclaimer, the term of this patent is extended or adjusted under 35 U.S.C. 154(b) by 0 days.

(21) Appl. No.: 09/367,609

(22) PCT Filed: Feb. 18, 1998

(86) PCT No.: PCT/IB98/00269

§ 371 Date: Aug. 16, 1999

§ 102(e) Date: Aug. 16, 1999

(87) PCT Pub. No.: WO98/37208

PCT Pub. Date: Aug. 27, 1998

(30) Foreign Application Priority Data

Feb. 19, 1997 (GB) .............................................. 9703406

(51) Int. Cl.$^7$ ........................... C12P 21/02; C12N 1/19; C12N 1/21; C12N 5/10; C12N 15/81
(52) U.S. Cl. ................. 435/69.1; 435/254.2; 435/252.3; 435/320.1; 435/325; 435/348; 435/471; 435/483
(58) Field of Search ............................. 435/69.1, 254.2, 435/254.21, 320.1, 325, 455, 471, 476, 483, 348, 252.3

(56) References Cited

U.S. PATENT DOCUMENTS 5,270,181 A 12/1993 McCoy et al.
5,831,049 A * 11/1998 Hillman et al. ............. 536/23.1

FOREIGN PATENT DOCUMENTS

| EP | 0 509 841 | 4/1992 |
| EP | 0 768 382 | 11/1996 |
| WO | WO 93/25676 | 12/1993 |
| WO | WO 94/02502 | 2/1994 |
| WO | WO 94/08012 | 4/1994 |
| WO | WO 95/16044 | 6/1995 |
| WO | WO 97/41207 | 11/1997 |

OTHER PUBLICATIONS

Hsu et al., Annals of the New York Academy of Sciences 721: 208–217, Engineering the assembly pathway of the baculovirus–insect cell expression system, 1994.*

Matthews et al., Nucleic Acids Research 20: 3821–3830, Thioredoxin regulates the DNA binding activity of NF–kappaB by reduction of a disulphide bond involving cysteine 62, 1992.*

Hayano et al., "Protein Disulfide Isomerase Mutant Lacking its Isomerase Activity Accelerates Protein Folding in the Cell", *FEBS Letters*, (1995) 377:505–511.

Humphreys et al., "Human Protein Disulfide Isomerase Functionally Complements a dsbA Mutation and Enhance the Yield of Pectate Lyase C in *Escherichia Coli*", *Journal of Biological Chemistry*, (1995) 270(47):28210–28215.

Humphreys et al., "Co–Expression of Human Protein Disulphide Isomerase (PDI) Can Increase the Yield of an Antibody FAB' Fragment Expressed in *Escherichia Coli*", *FEBS Letters*, (1996) 380:194–197.

Robinson et al., "Protein Disulfide Isomerase Overexpression Increases Secretion of Foreign Proteins in *Saccharomyces Cerevisiae*", *Bio/Technology*, (1994) 12:381–384.

Ostermeier et al., "Eukaryotic Protein Disulfide Isomerase Complements *Escherichia Coli* dsbA Mutants and Increases the Yield of a Heterologous Secreted Protein with Disulfide Bonds", *Journal of Biological Chemistry*, (1996) 271(18):10616–10622.

Watt et al., "Refolding of Recombinant *Pasteurella Haemolytica* A1 Glycoprotease expressed in an *Escherichia Coli* Thioredoxin Gene Fusion System", *Cell Stress & Chaperone*, (1997) 2(3):180–190.

* cited by examiner

Primary Examiner—Robert A. Schwartzman
(74) Attorney, Agent, or Firm—S. Maurice Valla; Alisa A. Harbin; Robert P. Blackburn

(57) ABSTRACT

An expression system which provides heterologous proteins expressed by a non-native host organism but which have native-protein-like biological activity and/or structure. Disclosed are vectors, expression hosts and methods for expressing the heterologous proteins. The expression system involves co-expression of protein factor(s) which is/are capable of catalyzing disulphide bond formation and desired heterologous protein(s). The expression system is presented using yeast cells as the preferred host, protein disulphide isomerase (PDI) and thioredoxin (TRX) as the preferred examples of the protein factors and HCV-E2$_{715}$ envelope glycoprotein and human FIGF as the preferred examples of the heterologous proteins.

28 Claims, 5 Drawing Sheets

1. S150/ Y-E2$_{715}$
2. S150-X21/ Y-E2$_{715}$
3. S150-PA1/ Y-E2$_{715}$
4. SX21-PA1/ Y-E2$_{715}$
5. S150-LyT/ Y-E2$_{715}$
6. S150-PA1

EXPRESSION OF HETEROLOGOUS PROTEINS

FIELD OF THE INVENTION

The present invention relates to an expression system which provides heterologous proteins expressed by a non-native host organism but which have native-protein-like biological activity and/or structure.

BACKGROUND TO THE INVENTION

Advances during the past decade in molecular biology and genetic engineering have made it possible to produce large amounts of protein products using heterologous expression systems.

The use of heterologous hosts for production of, for example, therapeutic proteins, can lead, however, to differences in the biological and/or structural properties of the recombinant product. Amongst the biochemical modifications that commonly occur to proteins during or following their synthesis in the cell, the formation of disulphide bonds is of relevance since this modification is coupled to the correct folding or assembly of disulphide-bonded proteins (reviewed by J. C. A. Bardwell and J. Beckwith, *Cell*, 74: 769–771, 1993; R. B. Freedman, in *Protein Folding*, T. E. Creighton (ed.), W. H. Freeman and Co., New York, pp. 455–539, 1992).

In bacteria and other host cells for example, under certain conditions, some heterologous proteins are precipitated within cells as "retractile" or "inclusion" bodies. Such refractile or inclusion bodies consist of dense masses of partially folded, reduced heterologous protein which is often in a form which is not biologically active (S. B. Storrs et al., *Protein Folding—American Chemical Society Symposium Series* 470, Chapter 15: 197–204, 1991). It is believed that the biological inactivity of natively-disulphide-bonded refractile or inclusion heterologous proteins is due to incorrect protein folding or assembly brought about by the non-formation or misformation of the disulphide bonds within the proteins. The biological inactivity of refractile or inclusion heterologous proteins due to the process of incorrect protein folding or assembly is believed to occur either before or after intracellular precipitation or during isolation of the proteins.

Moreover, very often the biological function of a protein is regulated or at least influenced by the state of oxidation of its sulphydryl groups. This is the case for some enzymatic activities where the reversibility and timing of oxidation of sulphydryl groups has been proposed as a physiological control mechanism.

There are numerous examples of disulphide-bonded proteins in the literature. For instance, most viral glycoproteins and some growth factors are known to be disulphide-bonded. In general, disulphide bonds are essential to correct protein folding. Examples of disulphide-bonded recombinant heterologous proteins that have been shown to be misfolded when expressed in, for example, yeast cells include hepatitis B virus large surface protein (Biemans et al., *DNA Cell Biol.*, 10: 191–200, 1991), α-1-antitrypsin (Moir and Dumais, *Gene*, 56: 209–217, 1987), and erythropoietin (Elliott et al., *Gene*, 79: 167–180, 1989). Examples of recombinant proteins expressed in, for example, insect or mammalian cells, for which disulphide bonds have been shown to be essential for correct protein folding, include granulocyte/macrophage colony stimulating factor (GM-CSF) (Kaushansky et al., *Proc. Natl. Acad. Sci. USA*, 86: 1213–1217, 1989), Friend erythroleukaemia virus (SFFV) glycoprotein gp55 (Gliniak et al., *J. Biol. Chem.*, 266: 22991–22997, 1991), glycoprotein of vesicular stomatitis virus (VSV-G) (Grigera et al., *J. Virol.*, 66: 3749–3757, 1992), pulmonary surfactant protein D (Crouch et al., *J. Biol. Chem.*, 269: 15808–15813, 1994), low density lipoprotein (LDL) receptor (Bieri et al., *Biochemistry*, 34: 13059–13065, 1995), insulin-like growth factor (Nahri et al., *Biochemistry*, 32: 5214–5221, 1993), and angiotensin-converting enzyme (ACE) (Sturrock et al., *Biochemistry*, 35: 9560–9566, 1996). It should be noted that in all these cases, heterologous protein expression in particular host cells was only used to produce sufficient quantities of the protein concerned to enable structural studies to be carried out.

Several protein factors which catalyze disulphide bond formation have been characterized. Protein disulphide isomerase (PDI) is an abundant, multifunctional protein found in the lumen of the endoplasmic reticulum (ER) that promotes proper formation of disulphide bonds in secretory and cell surface proteins (LaMantia et al., *Proc. Natl. Acad. Sci. USA*, 88: 4453–4457, 1991; Farquhar et al., *Gene*, 108: 81–89, 1991; Freedman, *Cell*, 57: 1069–1072, 1989; Laboissière et al., *J. Biol. Chem.*, 270: 28006–28009, 1995).

A similar function, but in a different cellular compartment, has been ascribed to another small, ubiquitous protein, thioredoxin (TRX) (Gan, *J. Biol. Chem.*, 266: 1692–1696, 1991; Muller, *J. Biol. Chem.*, 266: 9194–9202, 1991; Chivers et al., *EMBO J.*, 15: 2659–2667, 1996), that has an active-site sequence similar to that of PDI. Thioredoxins are cytosolic polypeptides capable of catalyzing the reduction of disulphides using glutathione as a reductant (Holmgren, *J. Biol. Chem.*, 264: 13963–13966, 1989). It has been postulated that thioredoxin may also be involved in the reduction of prematurely formed disulphides in proteins that have entered the ER. Since the biological activity of a number of key enzymes involved in crucial metabolic pathways depends on the cytosolic redox system, it is plausible that TRX plays a relevant role in the modification of proteins involved in folding in cellular compartments other than the cytosol.

In the numerous organisms, for example, bacteria, yeast, mammalian cells and insect cells, which have been genetically manipulated to (over)express heterologous proteins, the problem encountered with most expression systems is the inability to express proteins which are biologically active.

SUMMARY OF THE INVENTION

It now appears that due to the lack of or inefficient amount of the enzymes necessary for correct folding or assembly of heterologous proteins in non-native expression hosts, such expressed heterologous proteins are often not biologically active and/or have an incorrect protein structure.

The present invention overcomes this problem and allows for the expression of biologically active and/or correctly structured heterologous proteins in non-native expression hosts.

It has now been found that expression cassettes encoding PDI or TRX can be used to transform a host organism thereby making it capable of overexpressing PDI or TRX. Preferably, the host organism is yeast. Yeast cells, for example, overexpressing these proteins can subsequently or simultaneously be transformed with expression vectors encoding one or more desirable heterologous proteins. The heterologous proteins expressed in such PDI/TRX-transformed yeast cells are in a properly-folded, biologically active form due to the disulphide bond formation activity of the PDI or TRX enzymes co-expressed in the same cell.

Such systems for producing biologically active heterologous proteins can be advantageously used for the production of, for example, proteins for human or veterinary therapeutic and/or diagnostic use or other proteins of commercial or research interest. The correct and optimum biological activity effected by the methods of the present invention is paramount in producing, for example, effective drugs and diagnostic reagents.

PDI overexpression in *Saccharomyces cerevisiae* has been found to enhance the secretion of human platelet-derived growth factor B homodimer (PDGF-BB) into the culture medium (Robinson et al., *Bio/Technology*, 12: 381–384, 1994).

In the present invention an increased level of heterologous protein folding efficiency in cells has been demonstrated.

According to a first aspect of the invention there is provided a vector comprising an expression cassette comprising a DNA sequence encoding a protein capable of catalyzing disulphide bond formation.

Such a vector desirably results in (over)expression of the protein in a transformed host cell, thus providing the conditions for correct heterologous protein folding.

The protein may be any protein capable of catalyzing disulphide bond formation and is preferably protein disulphide isomerase (PDI) or thioredoxin (TRX) or a combination thereof. The genes encoding PDI and TRX are preferably obtained from yeast, more preferably from *S. cerevisiae*. However, the sources of PDI and TRX can also include, for example, human wild-type and mutant cDNA sequences.

As used herein, the term "expression cassette" connotes an DNA sequence comprising at least a structural DNA sequence encoding a protein and appropriate expression and optionally control sequences to facilitate expression of the structural DNA sequence.

The vector may comprise more than one DNA sequence encoding a protein which is capable of catalyzing disulphide bond formation, in one or more expression cassettes. The DNA sequences may be repeats of the same DNA sequence or may encode different proteins capable of catalyzing disulphide bond formation. Providing multiple copies of DNA sequences of the same or different proteins capable of catalyzing disulphide bond formation represents one way of achieving the desirable overexpression of the proteins and thus achieving the advantageous and inventive technical effect.

The expression cassette may also comprise a DNA sequence encoding a leader peptide for secretion fused to the 5' end of the gene coding for the protein capable of catalyzing disulphide bond formation. In so doing, the construct desirably results in (1) (over)expression of the protein in the transformed cell, and (2) localisation of the (over)expressed protein in the ER, and/or other secretory compartments, where it can exert its function, thus providing the conditions for correct heterologous protein folding.

The vector of the first aspect of the invention may also further comprise an expression cassette comprising DNA sequence(s) encoding one or more heterologous proteins. Preferably, the heterologous protein is hepatitis C virus (HCV) $E2_{715}$ envelope glycoprotein or human c-fos-induced growth factor (FIGF).

The vector of the first aspect of the invention may be integrative or episomal when transformed into a host organism. Preferably the vector is capable of integration into the host organism.

According to a second aspect of the invention there is provided a host organism transformed with a vector according to the first aspect of the invention.

Again, multiple copies of the vector may be present either as episomal vectors or integrated in the host organism genome to assist (over)expression of the protein capable of catalyzing disulphide bond formation.

According to a third aspect of the invention there is provided a host organism of the second aspect of the invention further transformed with a vector comprising an expression cassette comprising DNA sequence(s) encoding one or more heterologous proteins. This further vector may be integrative or episomal when transformed into the host organism.

The host organism may be co-transfected with more than one vector which comprises an expression cassette comprising DNA sequence(s) encoding one or more heterologous proteins.

The host organism may be any host organism in which the expression of a heterologous protein is prone to incorrect disulphide bond formation.

The heterologous protein may be any protein not normally produced in the host organism and which would, in the absence of (over)expression of the protein capable of catalyzing disulphide bond formation, be produced in a form with incorrect disulphide bonds. Preferably, the heterologous protein is HCV $E2_{715}$ envelope glycoprotein or human FIGF.

Preferably, the host organism according to the second and third aspects of the invention is yeast and more preferably *S. cerevisiae*.

According to a fourth aspect of the invention there is provided a method of producing a host organism according to the second aspect of the invention, comprising transforming a host organism with a vector of the first aspect of the invention.

According to a fifth aspect of the invention there is provided a method of producing a host organism according to the third aspect of the invention, comprising further transforming a host organism of the second aspect of the invention either subsequently or simultaneously with a vector comprising an expression cassette comprising DNA sequence(s) encoding one or more heterologous proteins.

According to a sixth aspect of the invention there is provided a method for expressing biologically active and/or correctly structured heterologous protein(s) in a host organism, comprising the steps of:
  (a) transforming a host organism with one or more vectors according to the first aspect of the present invention;
  (b) further transforming the host organism of step (a) either subsequently or simultaneously with one or more vectors comprising DNA sequence(s) encoding one or more heterologous proteins; and
  (c) culturing the host organism of step (b) in conditions suitable for expression of the one or more heterologous proteins.

According to a seventh aspect of the invention there is provided a method for expressing biologically active and/or correctly structured heterologous protein(s) in a host organism, comprising:
  (a) transforming a host organism according to the second aspect of the invention either subsequently or simultaneously with one or more vectors comprising DNA sequence(s) encoding one or more heterologous proteins; and (b) culturing the host organism of step (a) in conditions suitable for expression of the one or more heterologous proteins.

According to an eighth aspect of the invention there is provided a method for expressing biologically active and/or correctly structured heterologous protein(s) in a host organism, comprising the step of culturing a host organism transformed with one or more vectors according to the third aspect of the invention in conditions suitable for expression of the one or more heterologous proteins.

According to a ninth aspect of the invention there is provided a method for expressing HCV E2$_{715}$ envelope glycoprotein or human FIGF in a host organism.

According to a tenth aspect of the invention there is provided a method for the preparation of an immunogenic composition, comprising bringing HCV-E2$_{715}$ envelope glycoprotein or human FIGF produced by the method according to the ninth aspect of the invention into association with a pharmaceutically carrier and optionally an adjuvant.

DESCRIPTION OF SPECIFIC EMBODIMENTS

The practice of the present invention will employ, unless otherwise indicated, conventional techniques of molecular biology, microbiology, recombinant DNA, and immunology, which are within the skill of the art. Such techniques are explained fully in the literature (see, for example, Sambrook et al., *Molecular Cloning: A Laboratory Manual*, Second Edition, 1989; D. N Glover (ed.), *DNA Cloning*, Volumes I and II, 1985; M. J. Gait (ed.), *Oligonucleotide Synthesis*, 1984; B. D. Hames and S. J. Higgins (eds.), *Nucleic Acid Hybridization*, 1984; B. D. Hames and S. J. Higgins (eds.), *Transcription and Translation*, 1984; R. I. Freshney (ed.), *Animal Cell Culture*, 1986; *Immobilized Cells and Enzymes*, IRL Press, 1986; B. Perbal, *A Practical Guide to Molecular Cloning*, 1984; The series, *Methods in Enzymology*, Academic Press, Inc.; J. H. Miller and M. P. Calos (eds.), *Gene Transfer Vectors for Mammalian Cells*, Cold Spring Harbor Laboratory, 1987; Wu and Grossman (eds.) and Wu (ed.), *Methods in Enzymology, Volumes* 154 and 155, respectively; Mayer and Walker (eds.), *Immunochemical Methods in Cell and Molecular Biology*, Academic Press, London, 1987; Scopes, *Protein Purification: Principles and Practice*, Second Edition, Springer-Verlag, New York, 1987; and D. M. Weir and C. C. Blackwell (eds.), *Handbook of Experimental Immunology, Volumes* I–IV, 1986).

As mentioned above, examples of the protein capable of catalyzing disulphide bond formation that can be used in the present invention include polypeptides with minor amino acid variations from the amino acid sequence of the PDI or TRX protein specifically described.

A significant advantage of producing heterologous proteins by recombinant DNA techniques rather than by isolating and purifying a protein from natural sources is that equivalent quantities of the protein can be produced by using less starting material than would be required for isolating the protein from a natural source. Producing the protein by recombinant techniques also permits the protein to be isolated in the absence of some molecules normally present in cells. Indeed, protein compositions entirely free of any trace of human protein contaminants can readily be produced because the only human protein produced by the recombinant non-human host is the recombinant protein at issue. Potential viral agents from natural sources and viral components pathogenic to humans are also avoided.

Pharmaceutically acceptable carriers include any carrier that does not itself induce the production of antibodies harmful to the individual receiving the composition. Suitable carriers are typically large, slowly metabolized macromolecules such as proteins, polysaccharides, polylactic acids, polyglycolic acids, polymeric amino acids, amino acid copolymers, lipid aggregates (such as oil droplets or liposomes) and inactive virus particles. Such carriers are well known to those of ordinary skill in the art. Additionally, these carriers may function as immunostimulating agents (adjuvants).

Preferred adjuvants to enhance effectiveness of the composition include, but are not limited to: aluminum salts (alum) such as aluminium hydroxide, aluminium phosphate, aluminium sulphate etc., oil emulsion formulations, with or without other specific immunostimulating agents such as muramyl peptides or bacterial cell wall components, such as for example (1) MF59 (Published International patent application WO-A-90/14837, containing 5% Squalene, 0.5% Tween® 80, 0.5% Span® 85 (optionally containing various amounts of MTP-PE (see below), although not required) formulated into submicron particles using a microfluidizer such as Model 110Y microfluidizer (Microfluidics, Newton, Mass. 02164, USA), (2) SAF, containing 10% squalene, 0.4% Tween 80, 5% pluronic-blocked polymer L121, and thr-MDP (see below) either microfluidized into a submicron emulsion or vortexed to generate a larger particle size emulsion, and (3) RIBI™ adjuvant system (RAS) (Ribi Immunochem, Hamilton, Mont., USA) containing 2% Squalene, 0.2% Tween® 80 and one or more bacterial cell wall components from the group consisting of monophosphoryl lipid A (MPL), trehalose dimycolate (TDM), and cell wall skeleton (CWS) preferably MPL+CWS (Detox™), muramyl peptides such as N-acetyl-muramyl-L-threonyl-D-isoglutamine (thr-MDP), N-acetyl-normuramyl-L-alanyl-D-isoglutamine (nor-MDP), N-acetyl-muramyl-L-alanyl-D-isoglutaminyl-L-alanine-2-(1'-2'-dipalmitoyl-sn-glycero-3-hydroxyphosphoryloxy)-ethylamine (MTP-PE) etc., and cytokines, such as interleukins (IL-1, IL-2 etc.), macrophage colony stimulating factor (M-CSF), tumour necrosis factor (TNF) etc. Additionally, saponin adjuvants, such as Stimulon™ (Cambridge Bioscience, Worcester, Mass., USA) may be used or particles generated therefrom such as ISCOMS (immunostimulating complexes). Furthermore, complete Freunds Adjuvant (CFA) and Incomplete Freunds Adjuvant (IPA) may be used. Alum and MF59 are preferred.

The immunogenic compositions (e.g. the antigen, pharmaceutically acceptable carrier and adjuvant) typically will contain diluents, such as water, saline, glycerol, ethanol, etc. Additionally, auxiliary substances, such as wetting or emulsifying agents, pH buffering substances, and the like, may be present in such vehicles.

Typically, the immunogenic compositions are prepared as injectables, either as liquid solutions or suspensions; solid forms suitable for solution in, or suspension in, liquid vehicles prior to injection may also be prepared. The preparation also may be emulsified or encapsulated in liposomes for enhanced adjuvant effect as discussed above under pharmaceutically acceptable carriers.

Immunogenic compositions used as vaccines comprise an immunologically effective amount of the antigenic polypeptides, as well as any other of the above-mentioned components, as needed. By "immunologically effective amount", it is meant that the administration of that amount to an individual, either in a single dose or as part of a series, is effective for treatment or prevention. This amount varies depending upon the health and physical condition of the individual to be treated, the taxonomic group of individual to be treated (e.g., nonhuman primate, primate, etc.), the capacity of the individual's immune system to synthesize antibodies, the degree of protection desired, the formulation of the vaccine, the treating doctor's assessment of the medical situation, and other relevant factors. It is expected that the amount will fall in a relatively broad range that can be determined through routine trials.

The immunogenic compositions are conventionally administered parenterally, e.g. by injection either subcutaneously or intramuscularly. Additional formulations suitable for other modes of administration include oral and pulmonary formulations, suppositories and transdermal applications. Dosage treatment may be a single dose schedule or a multiple dose schedule. The vaccine may be administered in conjunction with other immunoregulatory agents.

The term "recombinant polynucleotide" as used herein intends a polynucleotide of genomic, cDNA, semisynthetic, or synthetic origin which, by virtue of its origin or manipulation: (1) is not associated with all or a portion of a polynucleotide with which it is associated in nature, (2) is linked to a polynucleotide other than that to which it is linked in nature, or (3) does not occur in nature.

The term "polynucleotide" as used herein refers to a polymeric form of nucleotides of any length, either ribonucleotides or deoxyribonucleotides. This term refers only to the primary structure of the molecule. Thus, this term includes double- and single-stranded DNA and RNA. It also includes known types of modifications, for example, labels which are known in the art, methylation, "caps", substitution of one or more of the naturally occurring nucleotides with an analogue, internucleotide modifications such as, for example, those with uncharged linkages (e.g., methyl phosphonates, phosphotriesters, phosphoamidates, carbamates, etc.) and with charged linkages (e.g., phosphorothioates, phosphorodithioates, etc.), those containing pendant moieties, such as, for example proteins (including, for example, nucleases, toxins, antibodies, signal peptides, poly-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide.

A "replicon" is any genetic element, e.g., a plasmid, a chromosome, a virus, a cosmid, etc. that behaves as an autonomous unit of polynucleotide replication within a cell; i.e., capable of replication under its own control. This may include selectable markers.

A "vector" is a replicon in which another polynucleotide segment is attached, so as to bring about the replication and/or expression of the attached segment.

"Control sequence" refers to polynucleotide sequences which are necessary to effect the expression of coding sequences to which they are ligated. The nature of such control sequences differs depending upon the host organism; in prokaryotes, such control sequences generally include promoter, ribosomal binding site, and transcription termination sequence; in eukaryotes, generally, such control sequences include promoters and transcription termination sequence. The term "control sequences" is intended to include, at a minimum, all components whose presence is necessary for expression, and may also include additional components whose presence is advantageous, for example, leader sequences and fusion partner sequences.

"Operably linked" refers to a juxtaposition wherein the components so described are in a relationship permitting them to function in their intended manner. A control sequence "operably linked" to a coding sequence is ligated in such a way that expression of the coding sequence is achieved under conditions compatible with the control sequences.

An "open reading frame" (ORF) is a region of a polynucleotide sequence which encodes a polypeptide; this region may represent a portion of a coding sequence or a total coding sequence.

A "coding sequence" is a polynucleotide sequence which is translated into a polypeptide, usually via MRNA, when placed under the control of appropriate regulatory sequences. The boundaries of the coding sequence are determined by a translation start codon at the 5'-terminus and a translation stop codon at the 3'-terminus. A coding sequence can include, but is not limited to, cDNA, and recombinant polynucleotide sequences.

"PCR" refers to the technique of polymerase chain reaction as described in Saiki et al., *Nature*, 324: 163, 1986; Scharf et al., *Science*, 233: 1076–1078, 1986; U.S. Pat. No. 4,683,195; and U.S. Pat. No. 4,683,202.

As used herein, x is "heterologous" with respect to y if x is not naturally associated with y in the identical manner; i.e., x is not associated with y in nature or x is not associated with y in the same manner as is found in nature.

"Homology" refers to the degree of similarity between x and y. The correspondence between the sequence from one form to another can be determined by techniques known in the art. For example, they can be determined by a direct comparison of the sequence information of the polynucleotide. Alternatively, homology can be determined by hybridization of the polynucleotides under conditions which form stable duplexes between homologous regions (for example, those which would be used prior to S1 digestion), followed by digestion with single-stranded specific nuclease(s), followed by size determination of the digested fragments.

As used herein, the term "polypeptide" refers to a polymer of amino acids and does not refer to a specific length of the product; thus, peptides, oligopeptides, and proteins are included within the definition of polypeptide. This term also does not refer to or exclude post expression modifications of the polypeptide, for example, glycosylations, acetylations, phosphorylations and the like. Included within the definition are, for example, polypeptides containing one or more analogues of an amino acid (including, for example, unnatural amino acids, etc.), polypeptides with substituted linkages, as well as other modifications known in the art, both naturally occurring and non-naturally occurring.

A polypeptide or amino acid sequence "derived from" a designated nucleic acid sequence refers to a polypeptide having an amino acid sequence identical to that of a polypeptide encoded in the sequence, or a portion thereof wherein the portion consists of at least 3–5 amino acids, and more preferably at least 8–10 amino acids, and even more preferably at least 11–15 amino acids, or which is immunologically identifiable with a polypeptide encoded in the sequence. This terminology also includes a polypeptide expressed from a designated nucleic acid sequence.

The protein may be used for producing antibodies, either monoclonal or polyclonal, specific to the protein. The methods for producing these antibodies are known in the art.

"Recombinant host cells", "host cells", "cells," "cell cultures", and other such terms denote, for example, microorganisms, insect cells, and mammalian cells, that can be, or have been, used as recipients for recombinant vector or other transfer DNA, and include the progeny of the original cell which has been transformed. It is understood that the progeny of a single parental cell may not necessarily be completely identical in morphology or in genomic or total DNA complement as the original parent, due to natural, accidental, or deliberate mutation. Examples for mammalian host cells include Chinese hamster ovary (CHO) and monkey kidney (COS) cells.

Specifically, as used herein, "cell line" refers to a population of cells capable of continuous or prolonged growth and division in vitro. Often, cell lines are clonal populations derived from a single progenitor cell. It is further known in the art that spontaneous or induced changes can occur in karyotype during storage or transfer of such clonal populations. Therefore, cells derived from the cell line referred to may not be precisely identical to the ancestral cells or cultures, and the cell line referred to includes such variants. The term "cell line" also includes immortalized cells. Preferably, cell lines include nonhybrid cell lines or hybridomas to only two cell types.

As used herein, the term "microorganism" includes prokaryotic and eukaryotic microbial species such as bacteria and fungi, the latter including yeast and filamentous fungi.

"Transformation", as used herein, refers to the insertion of an exogenous polynucleotide into a host cell, irrespective of the method used for the insertion, for example, direct uptake, transduction, f-mating or electroporation. The exogenous polynucleotide may be maintained as a non-integrated vector, for example, a plasmid, or alternatively, may be integrated into the host genome.

By "genomic" is meant a collection or library of DNA molecules which are derived from restriction fragments that have been cloned in vectors. This may include all or part of the genetic material of an organism.

By "cDNA" is meant a complementary DNA sequence that hybridizes to a complementary strand of DNA.

By "purified" and "isolated" is meant, when referring to a polypeptide or nucleotide sequence, that the indicated molecule is present in the substantial absence of other biological macromolecules of the same type. The term "purified" as used herein preferably means at least 75% by weight, more preferably at least 85% by weight, more preferably still at least 95% by weight, and most preferably at least 98% by weight, of biological macromolecules of the same type present (but water, buffers, and other small molecules, especially molecules having a molecular weight of less than 1000, can be present).

Once the appropriate coding sequence is isolated, it can be expressed in a variety of different expression systems; for example those used with mammalian cells, baculoviruses, bacteria, and yeast.

i. Mammalian Systems

Mammalian expression systems are known in the art. A mammalian promoter is any DNA sequence capable of binding mammalian RNA polymerase and initiating the downstream (3') transcription of a coding sequence (e.g. structural gene) into mRNA. A promoter will have a transcription initiating region, which is usually placed proximal to the 5' end of the coding sequence, and a TATA box, usually located 25–30 base pairs (bp) upstream of the transcription initiation site. The TATA box is thought to direct RNA polymerase II to begin RNA synthesis at the correct site. A mammalian promoter will also contain an upstream promoter element, usually located within 100 to 200 bp upstream of the TATA box. An upstream promoter element determines the rate at which transcription is initiated and can act in either orientation (Sambrook et al., "Expression of Cloned Genes in Mammalian Cells", in: *Molecular Cloning: A Laboratory Manual*, 2nd ed., 1989).

Mammalian viral genes are often highly expressed and have a broad host range; therefore sequences encoding mammalian viral genes provide particularly useful promoter sequences. Examples include the SV40 early promoter, mouse mammary tumour virus LTR promoter, adenovirus major late promoter (Ad MLP), and herpes simplex virus promoter. In addition, sequences derived from non-viral genes, such as the murine metallothioneih gene, also provide useful promoter sequences. Expression may be either constitutive or regulated (inducible), depending on the promoter can be induced with glucocorticoid in hormone-responsive cells.

The presence of an enhancer element (enhancer), combined with the promoter elements described above, will usually increase expression levels. An enhancer is a regulatory DNA sequence that can stimulate transcription up to 1000-fold when linked to homologous or heterologous promoters, with synthesis beginning at the normal RNA start site. Enhancers are also active when they are placed upstream or downstream from the transcription initiation site, in either normal or flipped orientation, or at a distance of more than 1000 nucleotides from the promoter (Maniatis et al., *Science*, 236: 1237, 1987; Alberts et al., *Molecular Biology of the Cell*, 2nd ed., 1989). Enhancer elements derived from viruses may be particularly useful, because they usually have a broader host range. Examples include the SV40 early gene enhancer [Dijkema et al., *EMBO J.*, 4: 761, 1985) and the enhancer/promoters derived from the long terminal repeat (LTR) of the Rous Sarcoma Virus (Gorman et al., *Proc. Natl. Acad. Sci. USA*, 79: 6777, 1982b) and from human cytomegalovirus (Boshart et al., *Cell*, 41: 521, 1985). Additionally, some enhancers are regulatable and become active only in the presence of an inducer, such as a hormone or metal ion (Sassone-Corsi and Borelli, *Trends Genet.*, 2: 215, 1986; Maniatis et al., Science, 236: 1237, 1987).

A DNA molecule may be expressed intracellularly in mammalian cells. A promoter sequence may be directly linked with the DNA molecule, in which case the first amino acid at the N-terminus of the recombinant protein will always be a methionine, which is encoded by the ATG start codon. If desired, the N-terminus may be cleaved from the protein by in vitro incubation with cyanogen bromide.

Alternatively, foreign proteins can also be secreted from the cell into the growth media by creating chimeric DNA molecules that encode a fusion protein comprised of a leader sequence fragment that provides for secretion of the foreign protein in mammalian cells. Preferably, there are processing sites encoded between the leader fragment and the foreign gene that can be cleaved either in vivo or in vitro. The leader sequence fragment usually encodes a signal peptide comprised of hydrophobic amino acids which direct the secretion of the protein from the cell. The adenovirus triparite leader is an example of a leader sequence that provides for secretion of a foreign protein in mammalian cells.

Usually, transcription termination and polyadenylation sequences recognized by mammalian cells are regulatory regions located 3' to the translation stop codon and thus, together with the promoter elements, flank the coding sequence. The 3' terminus of the mature mRNA is formed by site-specific post-transcriptional cleavage and polyadenylation (Birnstiel et al., *Cell*, 41: 349, 1985; Proudfoot and Whitelaw, "Termination and 3' end processing of eukaryotic RNA", in: *Transcription and Splicing* (eds. B. D. Hames and D. M. Glover), 1988; Proudfoot, *Trends Biochem. Sci.*, 14:

105, 1989). These sequences direct the transcription of an mRNA which can be translated into the polypeptide encoded by the DNA. Examples of transcription terminator/polyadenylation signals include those derived from SV40 (Sambrook et al., "Expression of cloned genes in cultured mammalian cells", in: *Molecular Cloning: A Laboratory Manual*, 1989).

Some genes may be expressed more efficiently when introns (also called intervening sequences) are present. Several cDNAs, however, have been efficiently expressed from vectors that lack splicing signals (also called splice donor and acceptor sites) (see, for example, Gothing and Sambrook, *Nature*, 293: 620, 1981). Introns are intervening noncoding sequences within a coding sequence that contain splice donor and acceptor sites. They are removed by a process called "splicing," following polyadenylation of the primary transcript (Nevins, *Ann. Rev. Biochem.*, 52: 441, 1983; Green, *Ann. Rev. Genet.*, 20: 671, 1986; Padgett et al., Ann. Rev. Biochem. 55: 1119, 1986; Krainer and Maniatis, "RNA splicing", in: *Transcription and Splicing* (eds. B. D. Hames and D. M. Glover), 1988).

Usually, the above-described components, comprising a promoter, polyadenylation signal, and transcription termination sequence are put together into expression constructs. Enhancers, introns with functional splice donor and acceptor sites, and leader sequences may also be included in an expression construct, if desired. Expression constructs are often maintained in a replicon, such as an extrachromosomal element (e.g., plasmids) capable of stable maintenance in a host, such as mammalian cells or bacteria. Mammalian replication systems include those derived from animal viruses, which require trans-acting factors to replicate. For example, plasmids containing the replication systems of papovaviruses, such as SV40 (Gluzman, *Cell*, 23: 175, 1981) or polyomaviruses, replicate to extremely high copy number in the presence of the appropriate viral T antigen. Additional examples of mammalian replicons include those derived from bovine papillomavirus and Epstein-Barr virus. Additionally, the replicon may have two replication systems, thus allowing it to be maintained, for example, in mammalian cells for expression and in a prokaryotic host for cloning and amplification. Examples of such mammalian-bacteria shuttle vectors include pMT2 (Kaufman et al., *Mol. Cell. Biol.*, 9: 946, 1989) and pHEBO (Shimizu et al., *Mol. Cell. Biol.*, 6: 1074, 1986).

The transformation procedure used depends upon the host to be transformed. Methods for introduction of heterologous polynucleotides into mammalian cells are known in the art and include dextran-mediated transfection, calcium phosphate precipitation, polybrene-mediated transfection, protoplast fusion, electroporation, encapsulation of -the polynucleotide(s) in liposomes, and direct microinjection of the DNA into nuclei.

Mammalian cell lines available as hosts for expression are known in the art and include many immortalized cell lines available from the American Type Culture Collection (ATCC), including but not limited to, Chinese hamster ovary (CHO) cells, HeLa cells, baby hamster kidney (BHK) cells, monkey kidney cells (COS), human hepatocellular carcinoma cells (e.g., Hep G2), and a number of other cell lines.

ii. Baculovirus Systems

The polynucleotide encoding the protein can also be inserted into a suitable insect expression vector, and is operably linked to the control elements within that vector. Vector construction employs techniques which are known in the art.

Generally, the components of the expression system include a transfer vector, usually a bacterial plasmid, which contains both a fragment of the baculovirus genome, and a convenient restriction site for insertion of the heterologous gene or genes to be expressed; a wild type baculovirus with a sequence homologous to the baculovirus-specific fragment in the transfer vector (this allows for the homologous recombination of the heterologous gene into the baculovirus genome); and appropriate insect host cells and growth media.

After inserting the DNA sequence encoding the protein into the transfer vector, the vector and the wild-type viral genome are transfected into an insect host cell where the vector and viral genome are allowed to recombine. The packaged recombinant virus is expressed and recombinant plaques are identified and purified. Materials and methods for baculovirus/insect cell expression systems -are commercially available in kit form from, inter alia, Invitrogen, San Diego, Calif., USA ("MaxBac" kit). These techniques are generally known to those skilled in the art and fully described in Summers and Smith, *Texas Agricultural Experiment Station Bulletin No.* 1555, 1987 (hereinafter "Summers and Smith").

Prior to inserting the DNA sequence encoding the protein into the baculovirus genome, the above-described components, comprising a promoter, leader (if desired), coding sequence of interest, and transcription termination sequence, are usually assembled into an intermediate transplacement construct (transfer vector). This construct may contain a single gene and operably linked regulatory elements; multiple genes, each with its owned set of operably linked regulatory elements; or multiple genes, regulated by the same set of regulatory elements. Intermediate transplacement constructs are often maintained in a replicon, such as an extrachromosomal element (e.g., plasmids) capable of stable maintenance in a host, such as a bacterium. The replicon will have a replication system, thus allowing it to be maintained in a suitable host for cloning and amplification.

Currently, the most commonly used transfer vector for introducing foreign genes into AcNPV is pAc373. Many other vectors, known to those of skill in the art, have also been designed. These include, for example, pVL985 (which alters the polyhedrin start codon from ATG to ATT, and which introduces a BamHI cloning site 32 basepairs downstream from the ATT; see Luckow and Summers, *Virology*, 17: 31, 1989).

The plasmid usually also contains the polyhedrin polyadenylation signal (Miller et al., *Ann. Rev. Microbiol.*, 42: 177, 1988) and a prokaryotic ampicillin-resistance (amp) gene and origin of replication for selection and propagation in *Escherichia coli*.

Baculovirus transfer vectors usually contain a baculovirus promoter. A baculovirus promoter is any DNA sequence capable of binding a baculovirus RNA polymerase and initiating the downstream (5' to 3') transcription of a coding sequence (e.g. structural gene) into mRNA. A promoter will have a transcription initiation region which is usually placed proximal to the 5' end of the coding sequence. This transcription initiation region usually includes an RNA polymerase binding site and a transcription initiation site. A baculovirus transfer vector may also have a second domain called an enhancer, which, if present, is usually distal to the structural gene. Expression may be either regulated or constitutive.

Structural genes, abundantly transcribed at late times in a viral infection cycle, provide particularly useful promoter sequences. Examples include sequences derived from the gene encoding the viral polyhedron protein (Friesen et al., "The Regulation of Baculovirus Gene Expression", in: *The*

*Molecular Biology of Baculoviruses* (ed. Walter Doerfler), 1986; and EPO Publ. Nos. 127 839 and 155 476) and the gene encoding the p10 protein (Vlak et al., *J. Gen. Virol.*, 69: 765, 1988).

DNA encoding suitable signal sequences can be derived from genes for secreted insect or baculovirus proteins, such as the baculovirus polyhedrin gene (Carbonell et al., *Gene*, 73: 409, 1988). Alternatively, since the signals for mammalian cell posttranslational modifications (such as signal peptide cleavage, proteolytic cleavage, and phosphorylation) appear to be recognized by insect cells, and the signals required for secretion and nuclear accumulation also appear to be conserved between the invertebrate cells and vertebrate cells, leaders of non-insect origin, such as those derived from genes encoding human α-interferon (Maeda et al., *Nature*, 315: 592, 1985), human gastrin-releasing peptide (Lebacq-Verheyden et al., *Mol. Cell. Biol.*, 8: 3129, 1988), human IL-2, Smith et al., *Proc. Natl. Acad. Sci. USA*, 82: 8404, 1985), mouse IL-3 (Miyajima et al., *Gene*, 58: 273, 1987) and human glucocerebrosidase (Martin et al., *DNA*, 7: 99, 1988), can also be used to provide for secretion in insects.

A recombinant polypeptide or polyprotein may be expressed intracellularly or, if it is expressed with the proper regulatory sequences, it can be secreted. Good intracellular expression of nonfused foreign proteins usually requires heterologous genes that ideally have a short leader sequence containing suitable translation initiation signals preceding an ATG start signal. If desired, methionine at the N-terminus may be cleaved from the mature protein by in vitro incubation with cyanogen bromide.

Alternatively, recombinant polyproteins or proteins which are not naturally secreted can be secreted from the insect cell by creating chimeric DNA molecules that encode a fusion protein comprised of a leader sequence fragment that provides for secretion of the foreign protein in insects. The leader sequence fragment usually encodes a signal peptide comprised of hydrophobic amino acids which direct the translocation of the protein into the endoplasmic reticulum.

After insertion of the DNA sequence and/or the gene encoding the expression product precursor of the protein, an insect cell host is co-transformed with the heterologous DNA of the transfer vector and the genomic DNA of wild-type baculovirus—usually by co-transfection. The promoter and transcription termination sequence of the construct will usually comprise a 2–5 kb section of the baculovirus genome. Methods for introducing heterologous DNA into the desired site in the baculovirus virus are known in the art (see Summers and Smith, supra; Smith et al., *Mol. Cell. Biol.*, 3: 2156, 1983; and Luckow and Summers, supra). For example, the insertion can be into a gene such as the polyhedrin gene, by homologous double crossover recombination; insertion can also be into a restriction enzyme site engineered into the desired baculovirus gene (Miller et al., *Bioessays*, 4: 91, 1989). The DNA sequence, when cloned in place of the polyhedrin gene in the expression vector, is flanked both 5' and 3' by polyhedrin-specific sequences and is positioned downstream of the polyhedrin promoter.

The newly formed baculovirus expression vector is subsequently packaged into an infectious recombinant baculovirus. Homologous recombination occurs at low frequency (between about 1% and about 5%); thus, the majority of the virus produced after co-transfection is still wild-type virus. Therefore, a method is necessary to identify recombinant viruses. An advantage of the expression system is a visual screen allowing recombinant viruses to be distinguished. The polyhedrin protein, which is produced by the native virus, is produced at very high levels in the nuclei of infected cells at late times after viral infection. Accumulated polyhedrin protein forms occlusion bodies that also contain embedded particles. These occlusion bodies, up to 15 µm in size, are highly refractile, giving them a bright shiny appearance that is readily visualized under the light microscope. Cells infected with recombinant viruses lack occlusion bodies. To distinguish recombinant virus from wild-type virus, the transfection supernatant is plaqued onto a monolayer of insect cells by techniques known to those skilled in the art. Namely, the plaques are screened under the light microscope for the presence (indicative of wild-type virus) or absence (indicative of recombinant virus) of occlusion bodies (Ansubel et al. (eds.), "*Current Protocols in Microbiology*", Vol. 2 at 16.8 (Supp. 10), 1990; Summers and Smith, supra; Miller et al., supra).

Recombinant baculovirus expression vectors have been developed for infection into several insect cells. For example, recombinant baculoviruses have been developed for, inter alia, *Aedes aegypti*, *Autographa californica*, *Bombyx mori*, *Drosophila melanogaster*, *Spodoptera frugiperda*, and *Trichoplusia ni* (PCT Pub. No. WO 89/046699; Carbonell et al., *J. Virol.*, 56: 153, 1985; Wright, *Nature*, 321: 718; 1986; Smith et al., *Mol. Cell. Biol.*, 3: 2156, 1983; and see generally, Fraser, et al., *In Vitro Cell. Dev. Biol.*, 25: 225, 1989).

Cells and cell culture media are commercially available for both direct and fusion expression of heterologous polypeptides in a baculovirus/expression system; cell culture technology is generally known to those skilled in the art (see, e.g., Summers and Smith, supra).

The modified insect cells may then be grown in an appropriate nutrient medium, which allows for stable maintenance of the plasmid(s) present in the modified insect host. Where the expression product gene is under inducible control, the host may be grown to high density, and expression induced. Alternatively, where expression is constitutive, the product will be continuously expressed into the medium and the nutrient medium must be continuously circulated, while removing the product of interest and augmenting depleted nutrients. The product may be purified by such techniques as chromatography, e.g., HPLC, affinity chromatography, ion exchange chromatography, etc.; electrophoresis; density gradient centrifugation; solvent extraction, or the like. As appropriate, the product may be further purified, as required, so as to remove substantially any insect proteins which are also secreted in the medium or result from lysis of insect cells, so as to provide a product which is at least substantially free of host debris, e.g., proteins, lipids and polysaccharides.

In order to obtain protein expression, recombinant host cells derived from the transformants are incubated under conditions which allow expression of the recombinant protein encoding sequence. These conditions will vary, dependent upon the host cell selected. However, the conditions are readily ascertainable to those of ordinary skill in the art, based upon what is known in the art.

iii. Bacterial Systems

Bacterial expression techniques are known in the art. A bacterial promoter is any DNA sequence capable of binding bacterial RNA polymerase and initiating the downstream (3") transcription of a coding sequence (e.g. structural gene) into mRNA. A promoter will have a transcription initiation region which is usually placed proximal to the 5' end of the coding sequence. This transcription initiation region usually includes an RNA polymerase binding site and a transcription initiation site. A bacterial promoter may also have a second domain called an operator, that may overlap an adjacent RNA polymerase binding site at which RNA synthesis begins. The operator permits negative regulated (inducible) transcription, as a gene repressor protein may bind the operator and thereby inhibit transcription of a specific gene. A Constitutive expression may occur in the absence of negative regulatory elements, such as the operator. In addition, positive regulation may be achieved by a gene activator protein binding sequence, which, if present is usually proximal (5') to the RNA polymerase binding sequence. An example of a gene activator protein is the catabolite activator protein (CAP), which helps initiate transcription of the lac operon in *E. coli* (Raibaud et al., *Ann. Rev. Genet.*, 18: 173, 1984). Regulated expression may therefore be either positive or negative, thereby either enhancing or reducing transcription.

Sequences encoding metabolic pathway enzymes provide particularly useful promoter sequences. Examples include promoter sequences derived from sugar metabolizing enzymes, such as galactose, lactose (lac) (Chang et al., *Nature*, 198: 1056, 1977), and maltose. Additional examples include promoter sequences derived from biosynthetic enzymes such as tryptophan (trp) (Goeddel et al., *Nuc. Acids Res.*, 8: 4057, 1980; Yelverton et al., *Nuc. Acids Res.*, 9: 731, 1981; U.S. Pat. No. 4,738,921; and EPO Publ. Nos. 036 776 and 121 775). The g-laotamase (bla) promoter system (Weissmann, "The cloning of interferon and other mistakes", in: *Interferon* 3 (ed. I. Gresser), 1981), and bacteriophage lambda PL (Shimatake et al., *Nature*, 292: 128, 1981) and T5 (U.S. Pat. No. 4,689,406) promoter systems also provide useful promoter sequences.

In addition, synthetic promoters which do not occur in nature also function as bacterial promoters. For example, transcription activation sequences of one bacterial or bacteriophage promoter may be joined with the operon sequences of another bacterial or bacteriophage promoter, creating a synthetic hybrid promoter (U.S. Pat. No. 4,551, 433). For example, the tac promoter is a hybrid trp-lac promoter comprised of both trp promoter and lac operon sequences that is regulated by the lac repressor (Amann et al., *Gene*, 25: 167, 1983; de Boer et al., *Proc. Natl. Acad. Sci. USA*, 80: 21, 1983). Furthermore, a bacterial promoter can include naturally occurring promoters of non-bacterial origin that have the ability to bind bacterial RNA polymerase and initiate transcription. A naturally occurring promoter of non-bacterial origin can also be coupled with a compatible RNA polymerase to produce high levels of expression of some genes in prokaryotes. The bacteriophage T7 RNA polymerase/promoter system is an example of a coupled promoter system (Studier et al., *J. Mol. Biol.*, 189: 113, 1986; Tabor et al., *Proc. Natl. Acad. Sci. USA*, 82: 1074, 1985). In addition, a hybrid promoter can also be comprised of a bacteriophage promoter and an *E. coli* operator region (EPO Publ. No. 267 851).

In addition to a functioning promoter sequence, an efficient ribosome binding site is also useful for the expression of foreign genes in prokaryotes. In *E. coli*, the ribosome binding site is called the Shine-Dalgarno (SD) sequence and includes an initiation codon (ATG) and a sequence. 3–9 nucleotides in length located 3–11 nucleotides upstream of the initiation codon (Shine et al., *Nature*, 254: 34, 1975). The SD sequence is thought to promote binding of mRNA to the ribosome by the pairing of bases between the SD sequence and the 3' and of *E. coli* 16S rRNA (Steitz et al., "Genetic signals and nucleotide sequences in messenger RNA", in: *Biological Regulation and Development: Gene Expression* (ed. R. F. Goldberger), 1979). To express eukaryotic genes and prokaryotic genes with weak ribosome-binding site (Sambrook et al., "Expression of cloned genes in *Escherichia coli*", in: *Molecular Cloning: A Laboratory Manual*, 1989).

A DNA molecule may be expressed intracellularly. A promoter sequence may be directly linked with the DNA molecule, in which case the first amino acid at the N-terminus will always be a methionine, which is encoded by the ATG start codon. If desired, methionine at the N-terminus may be cleaved from the protein by in vitro incubation with cyanogen bromide or by either in vivo on in vitro incubation with a bacterial methionine N-terminal peptidase (EPO Publ. No. 219 237).

Fusion proteins provide an alternative to direct expression. Usually, a DNA sequence encoding the N-terminal portion of an endogenous bacterial protein, or other stable protein, is fused to the 5' end of heterologous coding sequences. Upon expression, this construct will provide a fusion of the two amino acid sequences. For example, the bacteriophage lambda cell gene can be linked at the 5' terminus of a foreign gene and expressed in bacteria. The resulting fusion protein preferably retains a site for a processing enzyme (factor Xa) to cleave the bacteriophage protein from the foreign gene (Nagai et al., *Nature*, 309: 810, 1984). Fusion proteins can also be made with sequences from the lacZ (Jia et al., *Gene*, 60: 197, 1987), trpE (Allen et al., *J. Biotechnol.*, 5: 93, 1987; Makoff et al., *J. Gen. Microbiol.*, 135: 11, 1989), and Chey (EPO Publ. No. 324 647) genes. The DNA sequence at the junction of the two amino acid sequences may or may not encode a cleavable site. Another example is a ubiquitin fusion protein. Such a fusion protein is made with the ubiquitin region that preferably retains a site for a processing enzyme (e.g. ubiquitin specific processing-protease) to cleave the ubiquitin from the foreign protein. Through this method, native foreign protein can be isolated (Miller et al., *Bio/Technology* 7: 698, 1989).

Alternatively, foreign proteins can also be secreted from the cell by creating chimeric DNA molecules that encode a fusion protein comprised of a signal peptide sequence fragment that provides for secretion of the foreign protein in bacteria (U.S. Pat. No. 4,336,336). The signal sequence fragment usually encodes a signal peptide comprised of hydrophobic amino acids which direct the secretion of the protein from the cell. The protein is either secreted into the growth media (gram-positive bacteria) or into the periplasmic space, located between the inner and outer membrane of the cell (gram-negative bacteria). Preferably there are processing sites, which can be cleaved either in vivo or in vitro encoded between the signal peptide fragment and the foreign gene.

DNA encoding suitable signal sequences can be derived from genes for secreted bacterial proteins, such as the *E. coli* outer membrane protein gene (ompA) (Masui et al., in: *Experimental Manipulation of Gene Expression*, 1983; Ghrayeb et al., *EMBO J.*, 3: 2437, 1984) and the *E. coli* alkaline phosphatase signal sequence (phoA) (Oka et al., *Proc. Natl. Acad. Sci. USA*, 82: 7212, 1985). As an additional example, the signal sequence of the alpha-amylase gene from various Bacillus strains can be used to secrete heterologous proteins from *B. subtilis* (Palva et al., *Proc. Natl. Acad. Sci. USA*, 79: 5582, 1982; EPO Publ. No. 244 042).

Usually, transcription termination sequences recognized by bacteria are regulatory regions located 3' to the translation stop codon, and thus together with the promoter flank the coding sequence. These sequences direct the transcription of an mRNA which can be translated into the polypeptide encoded by the DNA. Transcription termination sequences frequently include DNA sequences of about 50 nucleotides capable of forming stem loop structures that aid in terminating transcription. Examples include transcription termination sequences derived from genes with strong promoters, such as the trp gene in *E. coli* as well as other biosynthetic genes.

Usually, the above described components, comprising a promoter, signal sequence (if desired), coding sequence of interest, and transcription termination sequence, are put together into expression constructs. Expression constructs are often maintained in a replicon, such as an extrachromosomal element (e.g., plasmids) capable of stable maintenance in a host, such as bacteria. The replicon will have a replication system, thus allowing it to be maintained in a prokaryotic host either for expression or for cloning and amplification. In addition, a replicon may be either a high or low copy number plasmid. A high copy number plasmid will generally have a copy number ranging from about 5 to about 200, and usually about 10 to about 150. A host containing a high copy number plasmid will preferably contain at least about 10, and more preferably at least about 20 plasmids. Either a high or low copy number vector may be selected, depending upon the effect of the vector and the foreign protein on the host.

Alternatively, the expression constructs can be integrated into the bacterial genome with an integrating vector. Integrating vectors usually contain at least one sequence homologous to the bacterial chromosome that allows the vector to integrate. Integrations appear to result from recombinations between homologous DNA in the vector and the bacterial chromosome. For example, integrating vectors constructed with DNA from various Bacillus strains integrate into the Bacillus chromosome (EPO Publ. No. 127 328). Integrating vectors may also be comprised of bacteriophage or transposon sequences.

Usually, extrachromosomal and integrating expression constructs may contain selectable markers to allow for the selection of bacterial strains that have been transformed. Selectable markers can be expressed in the bacterial host and may include genes which render bacteria resistant to drugs such as ampicillin, chloramphenicol, erythromycin, kanamycin (neomycin), and tetracycline (Davies et al., *Ann. Rev. Microbiol.*, 32: 469, 1978). Selectable markers may also include biosynthetic genes, such as those in the histidine, tryptophan, and leucine biosynthetic pathways.

Alternatively, some of the above described components can be put together in transformation vectors. Transformation vectors are usually comprised of a selectable marker that is either maintained in a replicon or developed into an integrating vector, as described above.

Expression and transformation vectors, either extrachromosomal replicons or integrating vectors, have been developed for transformation into many bacteria. For example, expression vectors have been developed for, inter alia, the following bacteria: *B. subtilis* (Palva et al., *Proc. Natl. Acad. Sci. USA*, 79: 5582, 1982; EPO Publ. Nos. 036 259 and 063 953; PCT Publ. No. WO 84/04541), *E. coli* (Shimatake et al., *Nature*, 292: 128, 1981; Amann et al., *Gene*, 40: 183, 1985; Studier et al., *J. Mol. Biol.*, 189: 113, 1986; EPO Publ. Nos. 036 776, 136 829 and 136 907), *Streptococcus cremoris* (Powell et al., *Appl. Environ. Microbiol.*, 54: 655, 1988); *Streptococcus lividans* (Powell et al., *Appl. Environ. Microbiol.*, 54: 655, 1988), and *Streptomyces lividans* (U.S. Pat. No. 4,745,056).

Methods of introducing exogenous DNA into bacterial hosts are well-known in the art, and usually include either the transformation of bacteria treated with $CaCl_2$ or other agents, such as divalent cations and DMSO. DNA can also be introduced into bacterial cells by electroporation. Transformation procedures usually vary with the bacterial species to be transformed (see, e.g., Masson et al., *FEMS Microbiol. Lett.*, 60: 273, 1989; Palva et al., *Proc. Natl. Acad. Sci. USA*, 79: 5582, 1982; EPO Publ. Nos. 036 259 and 063 953; PCT Publ. No. WO 84/04541 [Bacillus], Miller et al., *Proc. Natl. Acad. Sci. USA*, 8: 856, 1988; Wang et al., *J. Bacteriol.*, 172: 949, 1990 (Campylobacter], Cohen et al., *Proc. Natl. Acad. Sci. USA*, 69: 2110, 1973; Dower et al., *Nuc. Acids Res.*, 16: 6127, 1988; Kushner, "An improved method for transformation of *Escherichia coli* with ColE1-derived plasmids", in: *Genetic Engineering: Proceedings of the International Symposium on Genetic Engineering* (eds. H. W. Boyer and S. Nicosia), 1978; Mandel et al., *J. Mol. Biol.*, 53: 159, 1970; Taketo, *Biochim. Biophys. Acta*, 949: 318, 1988 [Escherichia], Chassy et al., *FEMS Microbiol. Lett.*, 44: 173, 1987 [Lactobacillus], Fiedler et al., *Anal. Biochem*, 170: 38, 1988 [Pseudomonas], Augustin et al., *FEMS Microbiol. Lett.*, 66: 203, 1990 [Staphylococcus), Barany et al., *J. Bacteriol.*, 144: 698, 1980; Harlander, "Transformation of *Streptococcus lactis* by electroporation", in: *Streptococcal Genetics* (ed. J. Ferretti and R. Curtiss III), 1987; Perry et al., *Infec. Immun.*, 32: 1295, 1981; Powell et al., *Appl. Environ. Microbiol.* 54: 655, 1988; Somkuti et al., *Proc.* 4th Eur. Cong. Biotechnology, 1: 412, 1987 [Streptococcus]).

iv. Yeast Expression

Yeast expression systems are also known to one of ordinary skill in the art. A yeast promoter is any DNA sequence capable of binding yeast RNA polymerase and initiating the downstream (3') transcription of a coding sequence (e.g. structural gene) into mRNA. A promoter will have a transcription initiation region which is usually placed proximal to the 5' end of the coding sequence. This transcription initiation region usually includes an RNA polymerase binding site (the "TATA Box") and a transcription initiation site. A yeast promoter may also have a second domain called an upstream activator sequence (UAS), which, if present, is usually distal to the structural gene. The UAS permits regulated (inducible) expression. Constitutive expression occurs in the absence of a UAS. Regulated expression may be either positive or negative, thereby either enhancing or reducing transcription.

Yeast is a fermenting organism with an active metabolic pathway, therefore sequences encoding enzymes in the metabolic pathway provide particularly useful promoter sequences. Examples include alcohol dehydrogenase (ADH) (EPO Publ. No. 284 044), enolase, glucokinase, glucose-6-phosphate isomerase, glyceraldehyde-3-phosphatedehydrogenase (GAP or GAPDH), hexokinase, phosphofructokinase, 3-phosphoglyceratemutase, and pyruvate kinase (PyK) (EPO Publ. No. 329 203). The yeast PHO5 gene, encoding acid phosphatase, also provides useful promoter sequences (Myanohara et al., *Proc. Natl. Acad. Sci. USA*, 80: 1, 1983).

In addition, synthetic promoters which do not occur in nature also function as yeast promoters. For example, UAS sequences of one yeast promoter may be joined with the transcription activation region of another yeast promoter, creating a synthetic hybrid promoter. Examples of such hybrid promoters include the ADH regulatory sequence linked to the GAP transcription activation region (U.S. Pat. Nos. 4,876,197 and 4,880,734). Other examples of hybrid promoters include promoters which consist of the regulatory sequences of either the ADH2, GAL4, GAL10, or PHO5 genes, combined with the transcriptional activation region of a glycolytic enzyme gene such as GAP or PyK (EPO Publ. No. 164 556). Furthermore, a yeast promoter can include naturally occurring promoters of non-yeast origin that have the ability to bind yeast RNA polymerase and initiate transcription. Examples of such promoters include, inter alia, Cohen et al., *Proc. Natl. Acad. Sci. USA*, 77: 1078, 1980; Henikoff et al., *Nature*, 283: 835, 1981; Hollenberg et al., *Curr. Topics Microbiol. Immunol.*, 96: 119, 1981; Hollenberg et al., "The Expression of Bacterial Antibiotic Resistance Genes in the Yeast *Saccharomyces cerevisiae*", in: *Plasmids of Medical, Environmental and Commercial Importance* (eds. K. N. Timmis and A. Puhler), 1979; Mercerau-Puigalon et al., *Gene*, 11: 163, 1980; Panthier et al., *Curr. Genet.*, 2: 109, 1980.

A DNA molecule may be expressed intracellularly in yeast. A promoter sequence may be directly linked with the DNA molecule, in which case the first amino acid at the N-terminus of the recombinant protein will always be a methionine, which is encoded by the ATG start codon. If desired, methionine at the N-terminus may be cleaved from the protein by in vitro incubation with cyanogen bromide.

Fusion proteins provide an alternative for yeast expression systems, as well as in mammalian, baculovirus, and bacterial expression systems. Usually, a DNA sequence encoding the N-terminal portion of an endogenous yeast protein, or other stable protein, is fused to the 5' end of heterologous coding sequences. Upon expression, this construct will provide a fusion of the two amino acid sequences. For example, the yeast or human superoxide dismutase (SOD) gene, can be linked at the 5' terminus of a foreign gene and expressed in yeast. The DNA sequence at the junction of the two amino acid sequences may or may not encode a cleavable site (see, e.g., EPO Publ. No. 196 056). Another example is a ubiquitin fusion protein. Such a fusion protein is made with the ubiquitin region that preferably retains a site for a processing enzyme (e.g. ubiquitin-specific processing protease) to cleave the ubiquitin from the foreign protein. Through this method, therefore, native foreign protein can be isolated (see, e.g., PCT Publ. No. WO 88/024066).

Alternatively, foreign proteins can also be secreted from the cell into the growth media by creating chimeric DNA molecules that encode a fusion protein comprised of a leader sequence fragment that provide for secretion in yeast of the foreign protein. Preferably, there are processing sites encoded between the leader fragment and the foreign gene that can be cleaved either in vivo or in vitro. The leader sequence fragment usually encodes a signal peptide comprised of hydrophobic amino acids which direct the secretion of the protein from the cell.

DNA encoding suitable signal sequences can be derived from genes for secreted yeast proteins, such as the yeast invertase gene (EPO Publ. No. 012 873; JPO Publ. No. 62,096,086) and the A-factor gene (U.S. Pat. No. 4,588, 684). Alternatively, leaders of non-yeast origin, such as an interferon leader, exist that also provide for secretion in yeast (EPO Publ. No. 060 057).

A preferred class of secretion leaders are those that employ a fragment of the yeast alpha-factor gene, which contains both a "pre" signal sequence, and a "pro" region. The types of alpha-factor fragments that can be employed include the full-length pre-pro alpha factor leader (about 83 amino acid residues) as well as truncated alpha-factor leaders (usually about 25 to about 50 amino acid residues) (U.S. Pat. Nos. 4,546,083 and 4,870,008; EPO Publ. No. 324 274). Additional leaders employing an alpha-factor leader fragment that provides for secretion include hybrid alpha-factor leaders made with a presequence of a first yeast, but a pro-region from a second yeast alpha-factor. (See, e.g., PCT Publ. No. WO 89/02463).

Usually, transcription termination sequences recognized by yeast are regulatory regions located 3' to the translation stop codon, and thus together with the promoter flank the coding sequence. These sequences direct the transcription of an mRNA which can be translated into the polypeptide encoded by the DNA. Examples of transcription terminator sequence and other yeast-recognized termination sequences, such as those coding for glycolytic enzymes, are well known.

Usually, the above described components, comprising a promoter, leader (if desired), coding sequence of interest, and transcription termination sequence, are put together into expression constructs. Expression constructs are often maintained in a replicon, such as an extrachromosomal element (e.g., plasmids) capable of stable maintenance in a host, such as yeast or bacteria. The replicon may have two replication systems, thus allowing it to be maintained, for example, in yeast for expression and in a prokaryotic host for cloning and amplification. Examples of such yeast-bacteria shuttle vectors include YEp24 (Botstein, et al., *Gene*, 8: 17–24, 1979), pCl/1 (Brake, et al., *Proc. Natl. Acad. Sci. USA*, 81: 4642–4646, 1984), and YRp17 (Stinchcomb, et al., *J. Mol. Biol.*, 158: 157, 1982). In addition, a replicon may be either a high or low copy number plasmid. A high copy number plasmid will generally have a copy number ranging from about 5 to about 200, and usually about 10 to about 150. A host containing a high copy number plasmid will preferably have at least about 10, and more preferably at least about 20. Either a high or low copy number vector may be selected, depending upon the effect of the vector and the foreign protein on the host (see, e.g., Brake et al., supra).

Alternatively, the expression constructs can be integrated into the yeast genome with an integrating vector. Integrating vectors usually contain at least one sequence homologous to a yeast chromosome that allows the vector to integrate, and preferably contain two homologous sequences flanking the expression construct. Integrations appear to result from recombinations between homologous DNA in the vector and the yeast chromosome (Orr-Weaver et al., *Methods in Enzymol.*, 101: 228–245, 1983). An integrating vector may be directed to a specific locus in yeast by selecting the appropriate homologous sequence for inclusion in the vector (see Orr-Weaver et al., supra). One or more expression constructs may integrate, possibly affecting levels of recombinant protein produced (Rine et al., *Proc. Natl. Acad. Sci. USA*, 80: 6750, 1983). The chromosomal sequences included in the vector can occur either as a single segment in the vector, which results in the integration of the entire vector, or two segments homologous to adjacent segments in the chromosome and flanking the expression construct in the vector, which can result in the stable integration of only the expression construct.

Usually, extrachromosomal and integrating expression constructs may contain selectable markers to allow for the selection of yeast strains that have been transformed.

Selectable markers may include biosynthetic genes that can be expressed in the yeast host, such as ADE2, HIS4, LEU2, TRP1, and ALG7, and the G418 resistance gene, which confer resistance in yeast cells to tunicamycin and G418, respectively. In addition, a suitable selectable marker may also provide yeast with the ability to grow in the presence of toxic compounds, such as metal. For example, the presence of CUP1 allows yeast to grow in the presence of copper ions (Butt et al., *Microbiol. Rev.*, 51: 351, 1987).

Alternatively, some of the above described components can be put together into transformation vectors. Transformation vectors are usually comprised of a selectable marker that is either maintained in a replicon or developed into an integrating vector, as described above.

Expression and transformation vectors, either extrachromosomal replicons or integrating vectors, have been developed for transformation into many yeasts. For example, expression vectors have been developed for, inter alia, the following yeasts: Candida albicans (Kurtz et al., *Mol. Cell. Biol.*, 6: 142, 1986), *Candida maltose* (Kunze et al., *J. Basic Microbiol.*, 25: 141, 1985), *Hansenula polymorpha* (Gleeson et al., *J. Gen. Microbiol.*, 132: 3459, 1986; Roggenkamp et al., *Mol. Gen. Genet.*, 202: 302, 1986), *kluyveromyces fragilis* (Das et al., *J. Bacteriol.*, 158: 1165, 1984), *Kluyveromyces lactis* (De Louvencourt et al., *J. Bacteriol.*, 154: 737, 1983; van den Berg et al., *Bio/Technology*, 8: 135, 1990), *Pichia guillerimondii* (Kunze et al., *J. Basic Microbiol.*, 25: 141, 1985), *Pichia pastoris* (Cregg et al., Mol. Cell. Biol., 5: 3376, 1985; U.S. Pat. Nos. 4,837,148 and 4,929,555), *Saccharomyces cerevisiae* (Hinnen et al., *Proc. Natl. Acad. Sci. USA*, 75: 1929, 1978; Ito et al., *J. Bacteriol.*, 153: 163, 1983), *Schizosaccharomyces pombe* (Beach and Nurse, Nature, 300: 706, 1981), and *Yarrowia lipolytica* (Davidow et al., *Curr. Genet.*, 10: 39, 1985; Gaillardin et al., *Curr. Genet.*, 10: 49, 1985).

Methods of introducing exogenous DNA into yeast hosts are well-known in the art, and usually include either the transformation of spheroplasts or of intact yeast cells treated with alkali cations. Transformation procedures usually vary with the yeast species to be transformed (see, e.g., Kurtz et al., *Mol. Cell. Biol.*, 6: 142, 1986; Kunze et al., *J. Basic Microbiol.*, 25: 141, 1985 [Candida], Gleeson et al., *J. Gen. Microbiol.*, 132: 3459, 1986; Roggenkamp et al., *Mol. Gen. Genet.*, 202: 302, 1986 [Hansenula], Das et al., *J. Bacteriol.*, 158: 1165, 1984; De Louvencourt et al., *J. Bacteriol.*, 754: 737, 1983; Van den Berg et al., *Bio/Technology*, 8: 135, 1990 [Kluyveromyces], Cregg et al., *Mol. Cell. Biol.*, 5: 3376, 1985; Kunze et al., *J. Basic Microbiol.*, 25: 141, 1985; U.S. Pat. Nos. 4,837,148 and 4,929,555 [Pichia], Hinnen et al., *Proc. Natl. Acad. Sci. USA*, 75: 1929, 1978; Ito et al., *J. Bacteriol.*, 153: 163, 1983 [Saccharomyces], Beach and Nurse, *Nature*, 300: 706, 1981 [Schizosaccharomyces], and Davidow et al., *Curr. Genet.*, 10: 39, 1985; Gaillardin et al., *Curr. Genet.*, 10: 49, 1985 [Yarrowia]).

The present invention will now be illustrated by way of example with reference to the following figures.

Figure 1A:
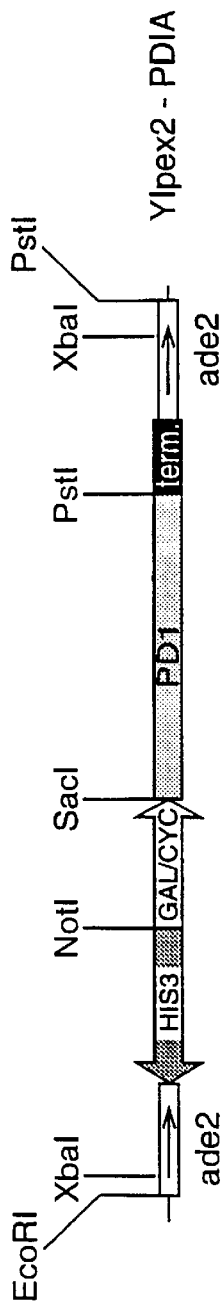
FIG. 1A is a linear restriction map of the integrative cassette for insertion of the expression cassette YIpex-PDI into the ADE2 chromosomal locus of *S. cerevisiae* showing the direction of transcription of PDI from the inducible GAL/CYC promoter (open arrow). Selected restriction sites are shown.
Figure 1B:
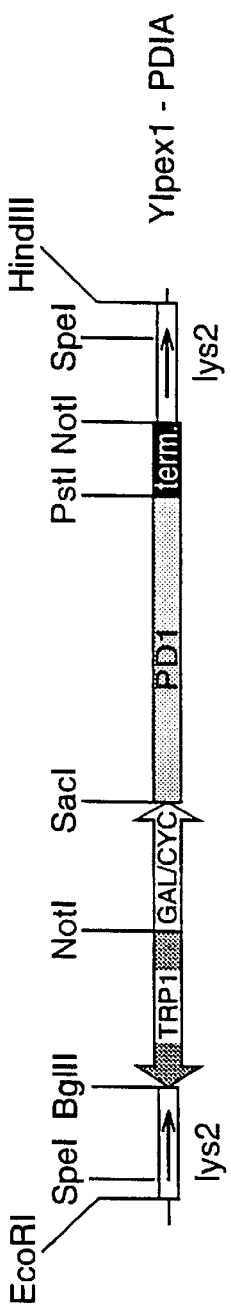
FIG. 1B is a restriction map of the integrative cassette for insertion of the same expression cassette depicted in FIG. 1A into the LYS2 chromosomal locus of *S. cerevisiae*.
Figure 1C:
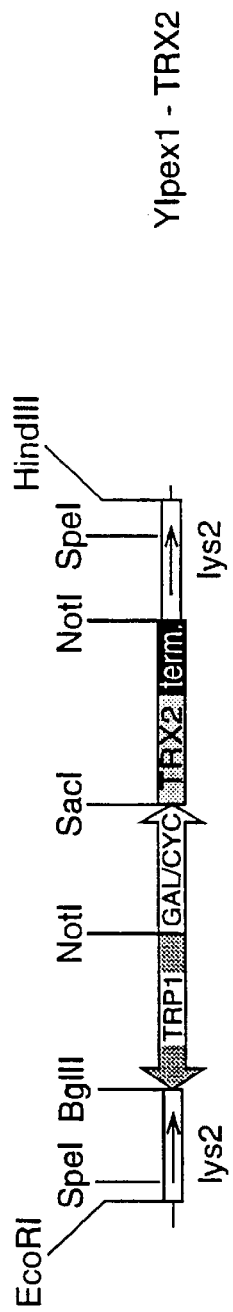
FIG. 1C is a restriction map of the LYS2 integrative cassette containing the *S. cerevisiae* TRX2 coding sequence inserted into the expression cassette.
Figure 1D:
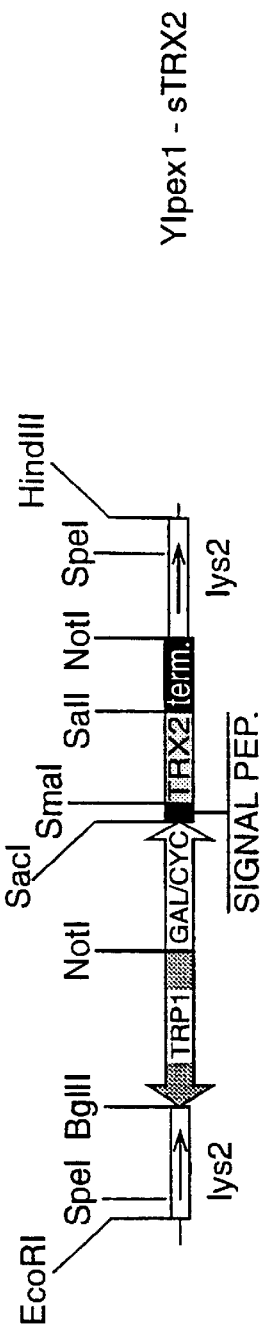
FIG. 1D is a restriction map of the LYS2 integrative cassette containing the *S. cerevisiae* TRX2 coding sequence inserted into the expression cassette fused in frame with the signal peptide sequence of YEpsec1.
Figure 2A:
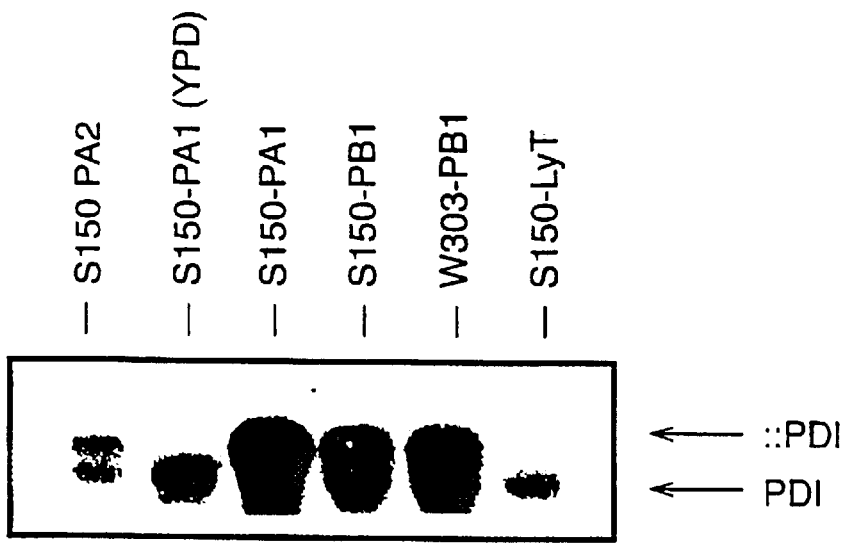
FIG. 2A shows a Northern blot analysis of RNA extracted from *S. cerevisiae* strains carrying chromosomal insertions of the PDI gene using a PDI-specific probe. The arrowheads indicate the transcript of the endogenous gene (PDI) and of the integrated PDI constructs (::PDI).
Figure 2B:
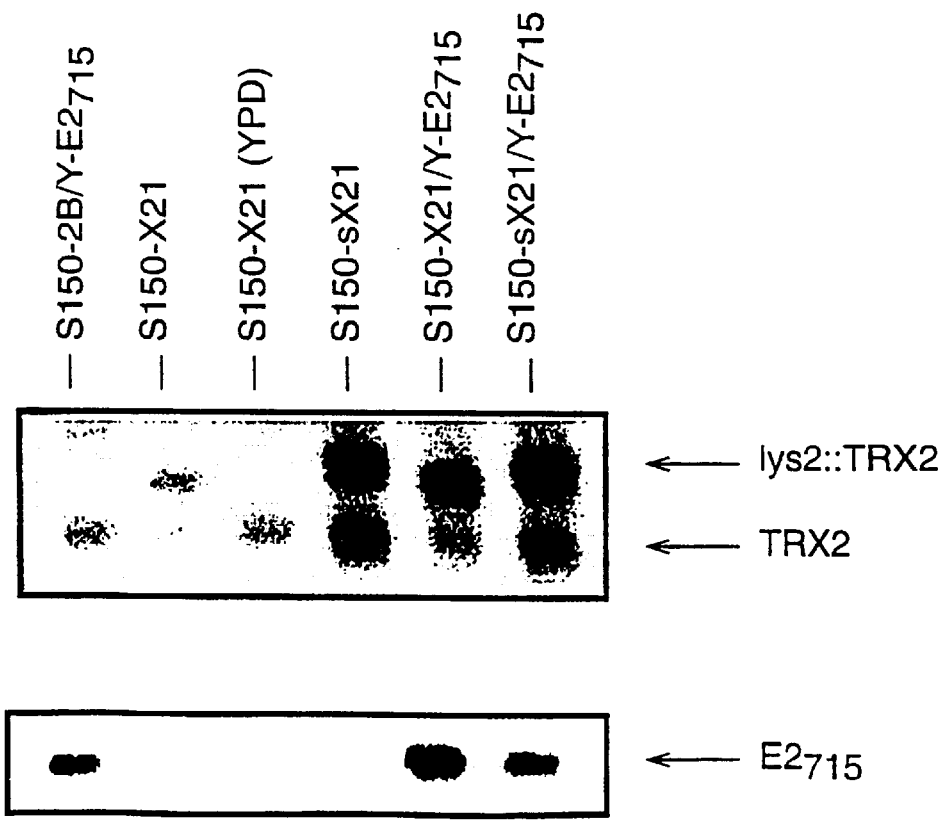

FIG. 2B shows RNA extracted from *S. cerevisiae* strains carrying chromosomal insertions of the TRX2 gene and the Y-E2$_{715}$ plasmid hybridised to a TRX2-specific (upper panel) and to an HCV-E2$_{715}$-specific probe (lower panel). The arrowheads indicate the transcript of the endogenous gene (TRX2), of the integrated TRX2 constructs (::TRX2) and of the HCV-E2$_{715}$ CDNA cloned in YEpsec1 (Y-E2$_{715}$).

Figure 3:
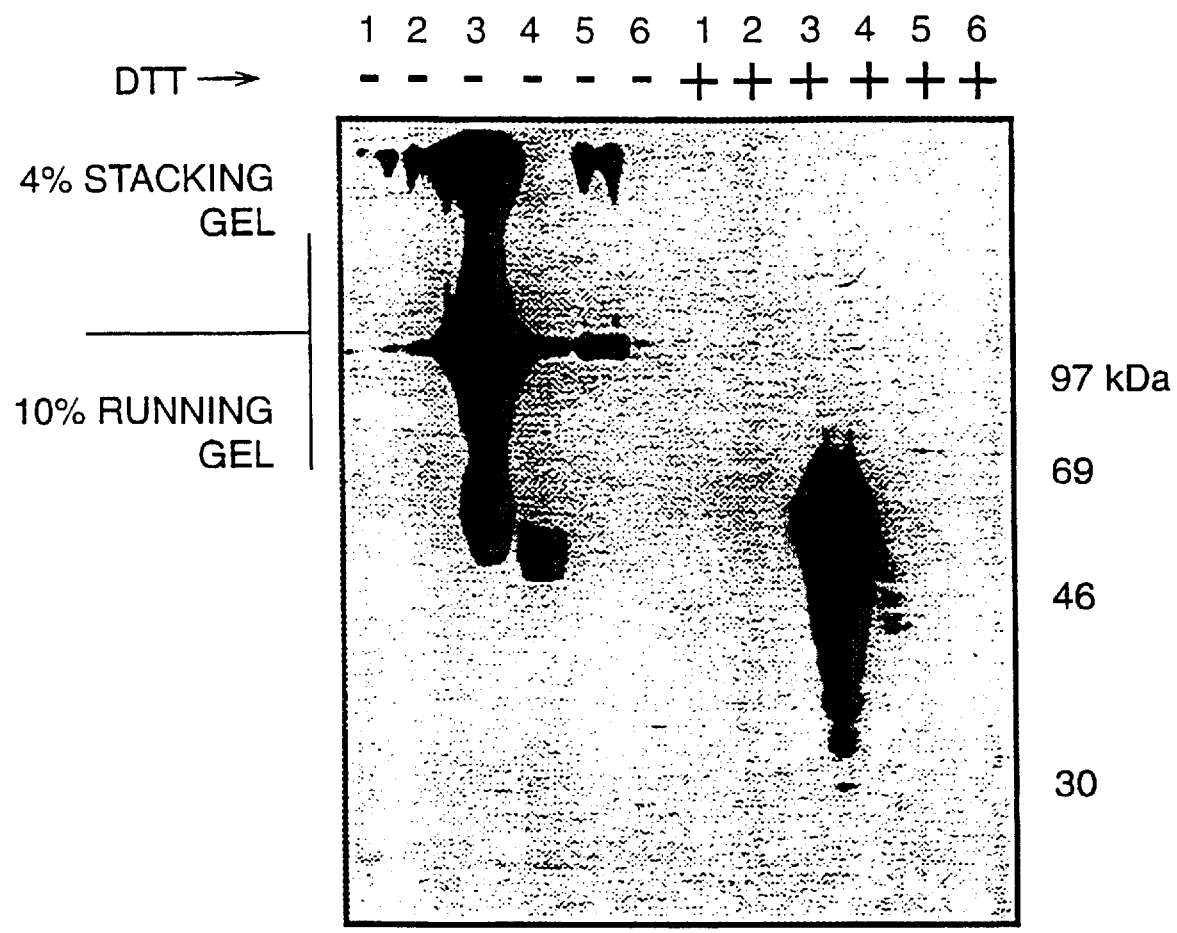

FIG. 3 shows a Western blot analysis of soluble proteins from cell extracts of modified yeast strains expressing HCV-E2$_{715}$ using an anti-E2 monoclonal antibody (mAb). Proteins were separated by SDS-PAGE in the presence (+DTT) or in the absence (−DTT) of a reducing agent.

Figure 4:
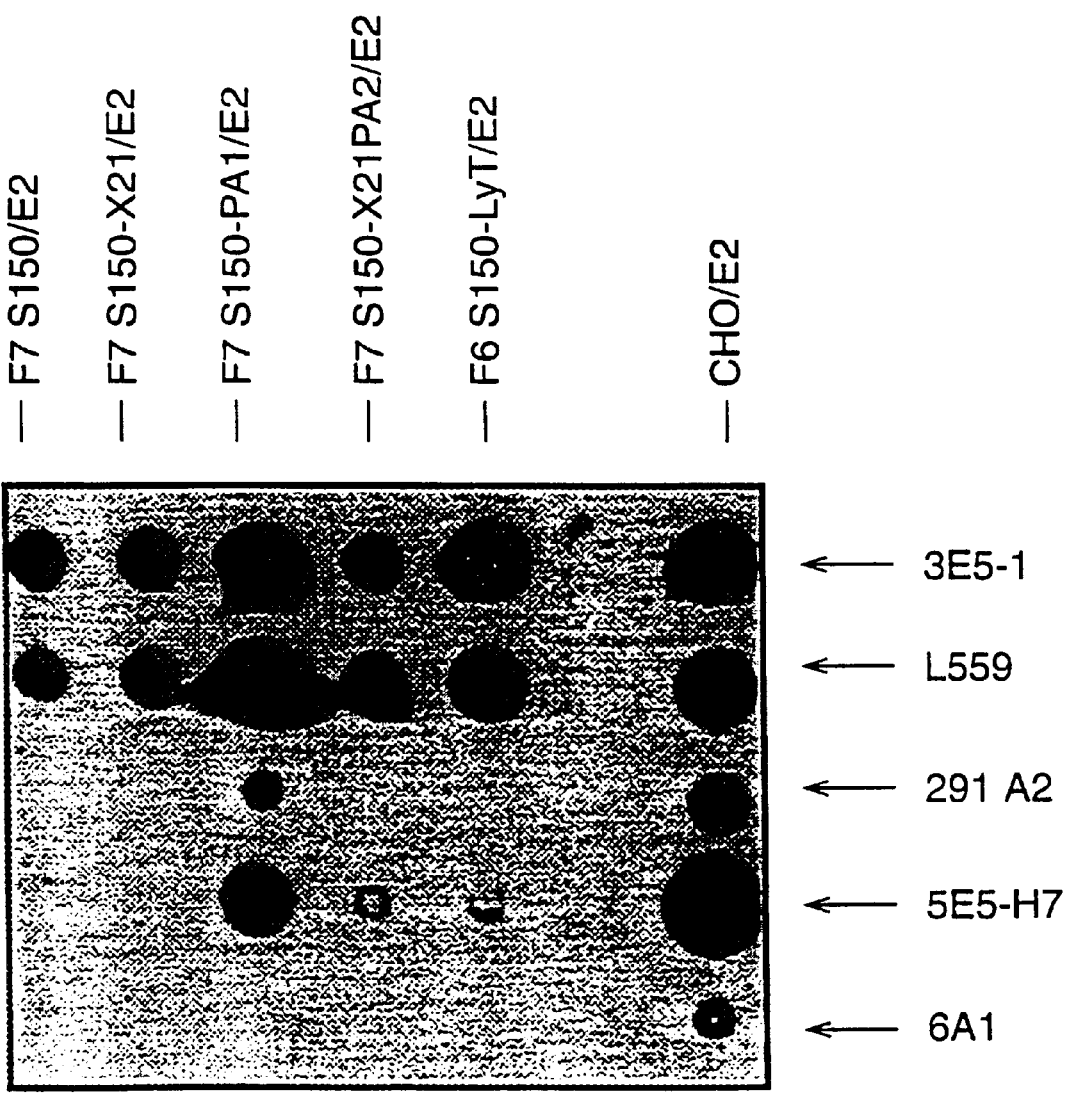

FIG. 4 shows a dot-blot analysis of affinity purified E2$_{715}$ (10 µg/dot) from the modified yeast strains. A mAb to HCV-E2$_{715}$ protein expressed in insect cells (3E5–1), a chimpanzee antiserum against HCV-E1E2 co-purified from HeLa cells (L559) (Choo et al., *Proc. Natl. Acad. Sci. USA*, 91: 1294–1298 1298, 1994) and three anti-E2$_{715}$-specific conformational mAbs (291A2, 5E5-H7, 6A1) (Rosa et al., *Proc. Natl. Acad. Sci. USA*, 93: 1759–1763, 1996) are used for immunoblotting.

Figure 5:
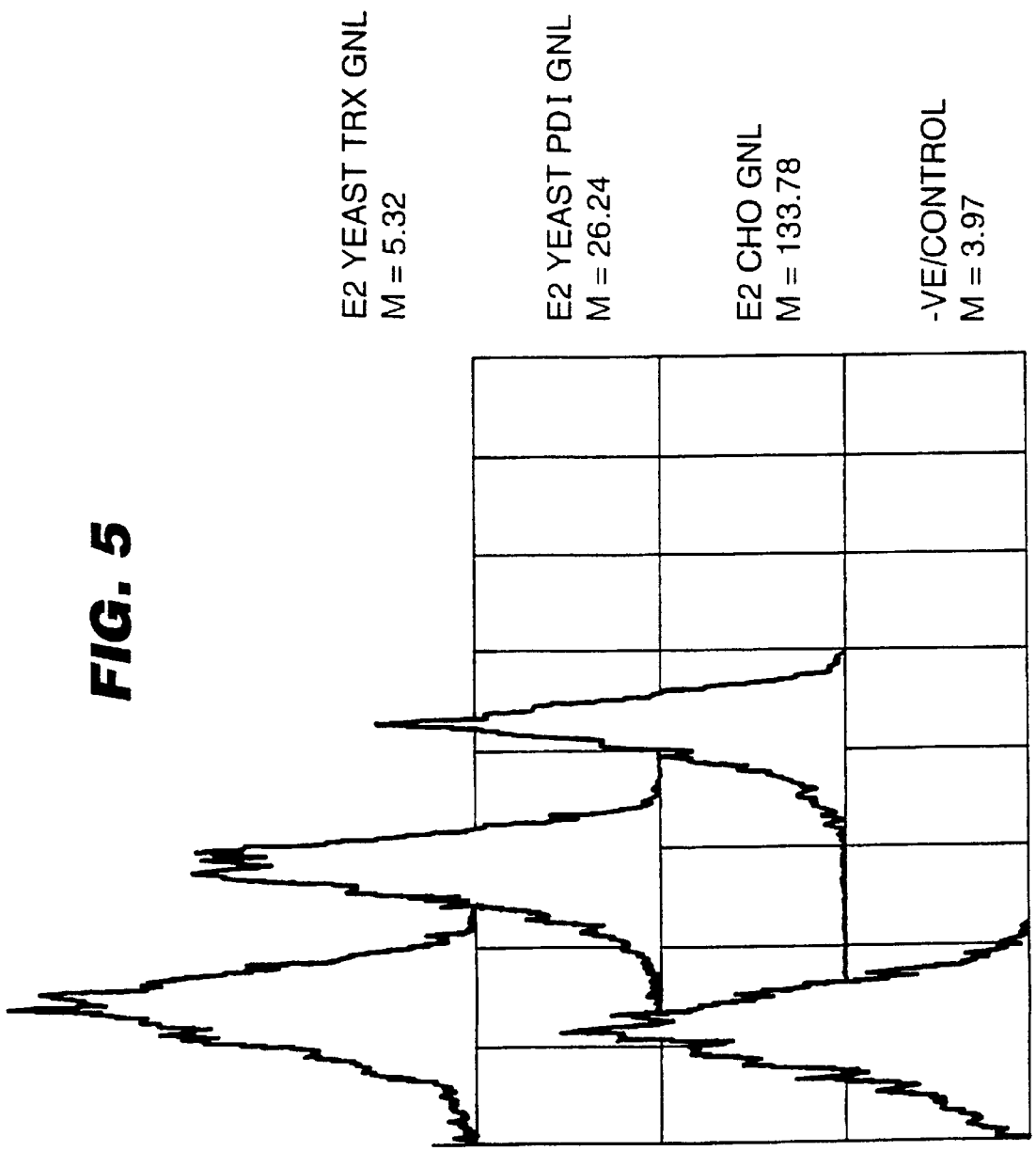

FIG. 5 shows a cell-bound fluorescence analysis of MOLT-4 cells pre-incubated with different forms of HCV-E2 protein expressed by modified yeast strains and CHO cells. The preincubated MOLT-4 cells are incubated with an anti-E2 mAb and, after incubating with fluorescent-labelled F(ab')$_2$ fragment IgG, binding to target cells is indirectly detected by flow cytometry as cell-bound fluorescence (relative cell number (y axis) versus mean fluorescence intensity (x axis)). Pre-incubated MOLT-4 cells (without HCV-E2 proteins) is the negative control.

EXAMPLES

Strains, Plasmids and Media

A description of the strains and plasmids used is presented in Table 1 and in FIGS. 1A–D. FIGS. 1A to 1D depict schematically the integrative cassettes used to modify the *S. cerevisiae* strains. The open boxes represent the *S. cerevisiae* chromosomal sequences ade2 (FIG. 1A) and lys2 (FIG. 1B–D) used for integration into the homologous chromosomal loci. The genetic markers used for selection of integrants (HIS3 and TRP1) are shown as hatched arrows, while the open arrow (GAL/CYC) indicates the promoter sequence. The black box (term) represents transcription termination sequences. The plasmid vector sequences are not shown.

TABLE 1

| S. cerevisiae strains | Genotype | integrative cassette |
|---|---|---|
| | Description of yeast strains | |
| W303-1B | MATα leu2.3-112 ura3-1 trp1-1 his3.11-15 ade2-1 can1-100 | none |
| W303-PB1 | MATα leu2.3-112 ura3-52 trp1-289 his3-Δ1 ade2-1 can1-100 lys2::TRP1::PDI | YIpex1-PDIB (lys2::TRP1) |
| S150-2B | MATα leu 2.3-112 ura 3-52 trp1-289 his3-Δ1 | none |
| S150-LyT | MATα leu2.3-112 ura3-52 trp1-289 his3-Δ1 lys2::TRP1::yex | YIpex1 (lys2::TRP1) |
| S150-PA1 | MATα leu2.3-112 ura3-52 trp1-289 his3-Δ1 lys2::TRP1::PDI | YIpex1-PDIA (lys2::TRP1) |
| S150-PB1 | MATα leu2.3-112 ura3-52 trp1-289 his3Δ1 lys2::TRP1::PDI | YIpex1-PDIB (lys2::TRP1) |
| S150-PA2 | MATα leu2.3-112 ura3-52 trp1-289 his3-Δ1 ade2::HIS3::PDI | YIpex2-PDIA (ade2::HIS3) |
| S150-X21 | MATα leu2.3-112 ura3-52 trp1-289 his3-Δ1 lys2::TRP1::TRX2 | YIpex1-TRX2 (lys2::TRP1) |
| S150-sX21 | MATα leu2.3-112 ura3-52 trp1-289 his3-Δ1 lys2::TRP1::sTRX2 | YIpex1-sTRX2 (lys2::TRP1) |
| SX21-PA2 | MATα leu2.3-112 ura3-52 trp1-289 his3-Δ1 lys2::TRP1::TRX2 ade::HIS3::PDI | YIpex1-TRX2 (lys2::TRP1) YIpex2-PDIA (ade2::HIS3) |
| | Description of Plasmids | |
| pUC18ycx | 1.238 bp of YEpsec 1 cloned in NotI site of pUC18Not | |
| pUC8-Lys | 1.318 bp LYS2 PCR fragment in EcoR1-HindIII sites of pUC8 | |
| pUC8-Ade | 1.059 bp ADE2 PCR fragment in EcoR1-PstI sites of pUC8 | |
| YIpLyT | 854 bp BglII PCR clone of TRP1 in BglII site of pUC8-Lys | |
| YIpAH | 931 bp BamHI PCR clone of HIS3 in BglII site of pUC8-Ade | |

The E. coli strain HB101 (F⁻ hsdS20 recA13 ara-14 proA2 lacY1 galK2 rpsL20 xyl-5 metl-1 supE44) was used for plasmid constructions. Transformation of E. coli cells and analysis of recombinant plasmids were carried out as described by Sambrook et al., Molecular Cloning: A Laboratory Manual, 2nd Edition, Cold Spring Harbor Laboratory, Cold Spring Harbor, N.Y., USA, 1989.

S. cerevisiae strains are grown at 30° C. in synthetic medium containing 2% carbon source and 0.67% yeast nitrogen base (Difco Laboratories, Detroit, Mich., USA) supplemented with the required amino acids (50 μg/ml) or in complete medium containing 2% glucose (YPD) or galactose (GalYP), 1% yeast extract, 2% peptone, 0.3% $KH_2PO_4$.

Plasmid Constructions and Genetic Manipulations

Restriction enzymes, T4 DNA ligase and other enzymes used for DNA and RNA manipulations are obtained from New England Biolabs (Hitchin, UK) or Boehringer Mannheim GmbH (Mannheim, Germany). PCR amplification of specific DNA fragments is performed with a Perkin Elmer Thermal Cycler (Norwalk, Conn., USA) using synthetic oligonucleotides. DNA sequencing is carried out using an Applied Biosystems (Norwalk, Conn., USA) model 373 DNA Sequencer. Total yeast DNA or RNA is extracted according to standard procedures (Sherman et al., Cold Spring Harbor Laboratory, Cold Spring Harbor, N.Y., USA, 1983). All other DNA manipulations are performed as described by Sambrook et al., supra. S. cerevisiae strains are transformed by the LiCl method (Rothstein, in: DNA Cloning (Glover, D. M. ed.), Vol. 11, pp. 45–66, IRL Press, 1985).

Two integrative cassettes are constructed for inserting the expression cassette into two different chromosomal loci of S. cerevisiae, LYS2 and ADE2. The integrative plasmid YIpLyT (Table 1) is obtained by cloning an EcoRI-HindIII PCR fragment comprising 1,318 bp of the S. cerevisiae LYS2 gene between the EcoRI and HindIII sites of plasmid pUC8. The resulting plasmid pUC8-Lys (Table 1) contains a unique BglII site located within the LYS2 sequence which is used for cloning of the S. cerevisiae selectable marker TRP1 obtained by PCR amplification of the TRP1 gene of plasmid YRp17. The integrative plasmid YIPAH (Table 1) is constructed by inserting into the EcoRI-PstI sites of pUC8 the 1,059 bp XbaI fragment of the S. cerevisiae ADE2 gene amplified by PCR adding an EcoRI site at the 5' end and a PstI site at the 3' end. The S. cerevisiae selectable marker HIS3 is amplified by PCR adding restriction sites BamHI-SpeI-NotI at the 5' end and a BamHI site at the 3' end. The HIS3 BamHI-digested PCR product is cloned into the unique BglII site of pUC8-Ade to give plasmid YIpAH.

The pUC18yex plasmid carrying the expression cassette is constructed by cloning a PCR-amplified NotI 1,238 bp fragment of plasmid YEpsec1 (Baldari et al., EMBO J., 6: 229–234, 1987; Galeotti et al., U.S. Pat. No. 5,432,082, Jul. 11, 1995), spanning the promoter to the terminator sequences, into the pUCl8 Not vector (Herrero et al., J. Bacteriol., 172: 6557–6567, 1990). Insertion of the sequence coding for S. cerevisiae PDI (LaMantia et al., Proc. Natl. Acad. Sci. USA, 88: 4453–4457, 1991) into the expression cassette of pUCyex is obtained by cloning a SacI-PstI PCR fragment into the SacI-PstI sites of pUc18yex. Similarly, the S. cerevisiae TRX2 coding sequence (Muller, J. Biol. Chem., 266: 9194–9202, 1991) is amplified by PCR adding a SacI site proximal to the ATG codon and a SalI site distal from the TGA stop codon and cloned into the SacI-SalI sites of pUC18yex. The sTRX version of the clone is obtained by substituting the SacI-ATG PCR primer with a SmaI PCR primer, which amplifies the TRX2 coding sequence from the second codon (TAG) in frame with the signal peptide sequence of pUC18yex, and cloning the PCR fragment into the SmaI-SalI sites of pUC18yex. All PCR clones are sequenced after cloning into the pUC18yex plasmid.

Vector YIpex2-PDI (FIG. 1A) is obtained by inserting the NotI-XbaI fragment of pUC18yex containing the PDI expression cassette into the NotI-SpeI sites of plasmid YIpAH (Table 1) in order to remove the XbaI site at the 3' end of the expression cassette and leave only the XbaI sites at the two extremities of the ADE2 integrative cassette. Transformation of strain S150-2B with XbaI-digested YIpex2-PDI results in integration of the PDI expression cassette into the ADE2 chromosomal locus of strain S150-PA2 (Table 1).

Cloning of the yex-PDI NotI fragment into the NotI site of YIpLyT (Table 1) gives rise to two plasmids containing the PDI expression cassette in opposite orientation with respect to the LYS2 integration locus. Plasmid YIpex1-PDIA (FIG. 1B) has the same orientation as YIpex2-PDI, while in plasmid YIpex1-PDIB the yex-PDI insert is in the opposite orientation. Transformation of S. cerevisiae with YIpex1-PDIA/B is carried out using SpeI-restricted integrative cassette. Strain S150-PA1 (Table 1) is an integrant carrying the yex-PDIA version, while strains W303-PB1 and S150-PB1 (Table 1) result from integration of yex-PDIB.

Plasmids YIpex1-TRX2 and YIpex1-sTRX2 (FIG. 1C and 1D) are generated by subcloning the NotI fragment of pUC18yex-TRX and pUC18yex-sTRX respectively into the NotI site of pUC18yex. The orientation of the cloned fragments chosen for producing S. cerevisiae integrants is the same as that of YIpex-PDIA. Integrants S150-X21 and SX21-PA2 -are obtained by transforming strains S150-2B and S150-PA2 (Table 1) with SpeI-digested YIpex1-TRX2, whereas transformation of S150-2B with YIpex1-sTRX2 generates integrant S150-sX21 (Table 1). The different S. cerevisiae integrants are subsequently transformed with the YEpsec1-E2$_{715}$ plasmid for expression of the HCV-E2$_{715}$ envelope glycoprotein in yeast.

In a similar method, the yeast strain (over)expressing PDI (S150-PA1, Table 1) has also been used to obtain human FIGF in a soluble form. The same factor is insoluble when expressed in the wild-type yeast strain (S150-2B).

Analysis of Transcription of the Integrated Genes

RNA from the different integrants grown under repressing (YPD) or inducing (GalYP) conditions is separated on a 2.2M formaldehyde-1.2% agarose gel, transferred to a nitrocellulose membrane and hybridized to $^{32}$P-labelled specific probes in order to determine if the site of integration and/or orientation of the expression cassette influences transcription of the integrated PDI or TRX2. Using a PDI-specific probe for Northern analysis of PDI integrants shows that transcription from the galactose-inducible promoter of integrated PDI is correctly regulated, i.e. repressed by growth in glucose medium (FIG. 1 A). Moreover, both the orientation of the transcription unit and the site of integration influence the level of transcription. A lower ratio between the transcript of integrated PDI and that of the endogenous gene is observed in integrants carrying the B (S150-PB1, W303-PB1) rather than the A (S150-PA1) orientation of the construct and integration in ade2 (S150-PA2) leads to an even greater reduction.

Analysis of transcription of the HCV-E2$_{715}$ CDNA cloned in YEpsec1 (Y-E2$_{715}$) in lys2::TRX2 and lys2::sTRX2 integrants grown in GalYP shows that the insertion of a galactose-regulated TRX2 gene in these strains does not influence the level of E2$_{715}$ mRNA, even though expression of both genes requires the same transcription factors (FIG. 2B).

overexpression of PDI and TRX2 Facilitates Folding of HCV-E2$_{715}$ in S. cerevisiae Cell extracts are prepared from yeast cultures by disrupting cells with glass beads in a Braün homogenizer (B. Braün Melsungen AG, Melsungen, Germany) for 20 s at 4° C. After disruption, the cell suspensions are diluted in PBS and affinity-purified (see below). Protein samples are analyzed by SDS-polyacrylamide gel electrophoresis (SDS-PAGE) as described by Laemmli (Laemmli, Nature, 227: 680–685, 1970) in LSB buffer (2% SDS, 10% glycerol, 200 mM DTT, 62.5 mM Tris-HCl, pH 6.8 and transferred to nitrocellulose membrane (Nitrobind, MSI, Westborough, Mass., USA) (Towbin et al., Proc. Natl. Acad. Sci. USA, 76: 4350–4354, 1979). The membrane is incubated in a buffer containing PBS, 3% milk powder and 0.1% Triton. A monoclonal antibody (mAb) to a linear epitope of HCV-E2$_{715}$ protein expressed in insect cells (3E5-1), two conformational mAbs (291A2 and 5E5-H7) and chimpanzee antiserum against HCV-E1E2 co-purified from HeLa cells (L559) (Choo et al., Proc. Natl. Acad. Sci. USA, 91: 1294–1298, 1994; Rosa et al., Proc. Natl. Acad. Sci. USA, 93: 1759–1763, 1996) are used for immunoblotting. Immunoblots are developed with enhanced chemiluminescence (ECL, Amersham, Arlington Heights, Ill., USA).

HCV-E2$_{715}$ is purified from yeast cultures by affinity chromatography using a lectin column (Galanthus nivalisagarose lectin (GNL); particular commercially available GNL used was GNA, Vector Laboratories Inc., Burlingame, Calif., USA). The column is equilibrated with PBS at 40 cm/h, washed with 0.9M NaCl in PBS and the glycoprotein is eluted by using 1M a-methyl-D-mannoside, 0.9M NaCl in PBS. The column fractions are dialysed against PBS, protein concentrations are determined using the Lowry method (Bio-Rad DC Protein Assay, Bio-Rad, Hercules, Calif., USA) and analyzed by dot-blot with monoclonal anti-E2 antibodies.

Western blot analysis of affinity-purified proteins from cell extracts of lys2: :TRX2, lys2: :PDI, lys2: :TRX2-ade2::PDI integrants expressing HCV-E2$_{715}$ reveals that a proportion of the E2$_{715}$ glycoprotein can enter the separating gel in the absence of DTT only in samples from integrants overexpressing PDI. The relative amount of glycoprotein entering the gel without a reducing agent appears to be even greater in the sample from the double integrant SX21-PA2 (FIG. 3).

Immunoblotting of undenatured E2$_{715}$ from the different yeast strains shows that the glycoprotein purified from the PDI integrant binds the 5E5-H7 and, at a lower extent, the 291A2 conformational antibodies (FIG. 4).

Different Forms of HCV-E2 Protein Expressed in Modified Yeast Strains Bind to MOLT-4 Cells HCV-E2 protein is expressed in nature in mammalian cells and binds human cells with high affinity. To investigate whether modified yeast-expressed E2 proteins has similar biological activity and can bind human cells, cells of the human T-cell lymphoma line, MOLT-4 are incubated at 4° C. with different forms of modified yeast-expressed E2 protein (8.7 µg/ml). As a positive control, CHO-expressed E2 protein is used at the same concentration. As a negative control, MOLT-4 cells are incubated in the absence of E2 proteins. Subsequently, the cellular pellet is incubated with mAb raised against E2. After incubation with phycoerythrin-labelled F(ab')$_2$ fragment goat anti-mouse IgG, binding to target cells is indirectly detected by flow cytometry as cell-bound fluorescence (FIG. 5).

As is shown in FIG. 5, the MOLT-4 cells pre-incubated with CHO-expressed HCV-E2 protein (E2 CHO GNL) have the highest mean fluorescence intensity (M=133.78) when compared to the MOLT-4 cells pre-incubated with modified yeast-expressed E2 proteins (M=26.24 (E2 Yeast PDI GNL); M=5.32 (E2 Yeast TRX GNL)). However, the MOLT-4 cells pre-incubated with modified yeast-expressed E2 protein nevertheless are higher in mean fluorescence intensity than the MOLT-4 cells pre-incubated with no E2 proteins (M=3.97 (-ve/Control)).

The binding of the different forms of the E2 protein to the MOLT-4 cells is influenced by the structure of the proteins. The CHO-expressed E2 protein has appropriately-formed disulphide bonds and is therefore correctly folded and biologically active. The consequence of this is a high binding affinity of the CHO-expressed E2 protein for the cell surfaces of the MOLT-4 cells, resulting in a high mean fluorescence intensity. Similarly, the modified yeast-expressed E2 proteins also appear to be biologically active since they bind MOLT-4 cells, thereby resulting in a higher mean fluorescence intensity compared to the negative control.

Although the mean fluorescence intensity (and therefore binding affinity for MOLT-4 cells) is lower for the modified yeast-expressed E2 proteins compared to the CHO-expressed E2 protein, non-modified yeast-expressed E2 protein (i.e. expressed in yeast cells without co-expression of PDI or TRX) is unable to bind MOLT-4 cells (see Rosa et al., Proc. Natl. Acad. Sci. USA, 93: 1759–1763, 1996; particularly lines 16 to 18 of Results paragraph on page 1760 and FIG. 1). Thus, the modified host expression system of the present invention can produce heterologous proteins of a similar biological activity and/or structure to the native proteins produced by their natural hosts.

What is claimed is:

1. A vector comprising:
    (i) an expression cassette comprising a DNA sequence encoding thioredoxin (TRX); and
    (ii) an expression cassette comprising DNA sequence(s) encoding one or more heterologous proteins;
        wherein said one or more heterologous proteins do(es) not form fusion protein(s) with said TRX.

2. A vector according to claim 1, wherein the heterologous protein is hepatitis C virus (HCV) $E2_{715}$ envelope glycoprotein or human c-fos-induced growth factor (FIGF).

3. A vector according to claim 1 wherein the vector is capable of integrating into the genome of a host organism.

4. A vector according to claim 1 wherein the vector further comprises DNA sequence(s) encoding one or more leader peptides for secretion to the endoplasmic reticulum (ER) and/or other secretory compartments.

5. A host organism transformed with one or more vectors according to any one of claims 1 or 2 to 4.

6. A method of producing a transformed organism, said method comprising transforming a host organism with one or more vectors according to any one of claims 1 or 2 to 4.

7. A host organism according to claim 5, wherein said organism is a yeast.

8. A method for expressing biologically active and/or correctly structured heterologous protein(s) in an organism, comprising the step of culturing a host organism transformed according to claim 5 in conditions suitable for expression of the heterologous protein(s).

9. A method according to claim 8 wherein said organism is a yeast.

10. A vector comprising:
    (i) an expression cassette comprising a DNA sequence encoding a protein that catalyzes disulphide bond formation; and
    (ii) an expression cassette comprising DNA sequence(s) encoding a heterologous protein selected from the group consisting of hepatitis C virus (HCV) $E2_{715}$ envelope glycoprotein and human c-fos-induced growth factor (FIGF);
wherein said heterologous protein, when expressed, is localised in the endoplasmic reticulum (ER) and/or other secretory compartments.

11. A vector according to claim 10, wherein the protein that catalyzes disulphide bond formation is protein disulphide isomerase (PDI).

12. A vector according to claim 10, wherein the vector further comprises DNA sequence(s) encoding one or more leader peptides for secretion to the ER and/or other secretory compartments.

13. A vector according to claim 10, wherein the vector is capable of integrating into the genome of a host organism.

14. A host organism transformed with one or more vectors according to any one of claims 10 to 13.

15. A method of producing a transformed organism, said method comprising transforming a host organism with one or more vectors according to any one of claims 10 to 13.

16. A host organism according to claim 14, wherein said organism is a yeast.

17. A method for expressing biologically active and/or correctly structured heterologous protein(s) in an organism, comprising the step of culturing an organism transformed according to claim 14 in conditions suitable for expression of said heterologous protein.

18. A method according to claim 15, wherein said host organism is a yeast.

19. A host organism transformed with:
    (i) one or more vectors comprising an expression cassette comprising a DNA sequence encoding a protein that catalyzes disulphide bond formation; and
    (ii) one or more vectors comprising an expression cassette comprising DNA sequence(s) encoding a heterologous protein selected from the group consisting of hepatitis C virus (HCV) $E2_{715}$ envelope glycoprotein and human c-fos-induced growth factor (FIGF);
wherein said heterologous protein, when expressed, is localized in the ER and/or other secretory compartments.

20. A host organism according to claim 19, wherein the protein that catalyzes disulphide bond formation is protein disulphide isomerase (PDI).

21. A host organism according to claim 19, wherein said protein that catalyzes disulphide bond formation is TRX, and wherein said heterologous protein when expressed, does not form fusion protein(s) with said TRX.

22. A host organism according to any one of claims 19 to 21, wherein said organism is a yeast.

23. A method for expressing biologically active and/or correctly structured heterologous protein(s) in an organism, comprising the step of culturing an organism transformed according to any one of claims 19 to 21 in conditions suitable for expression of said heterologous protein.

24. A method for expressing biologically active and/or correctly structured heterologous protein(s) in an organism, comprising the step of culturing an organism transformed according to claim 22 in conditions suitable for expression of said heterologous protein.

25. A method of producing a transformed organism, said method comprising:
    (i) transforming a host organism with one or more vectors comprising an expression cassette comprising a DNA sequence encoding a protein that catalyzes disulphide bond formation; and
    (ii) either simultaneously or sequentially further transforming said host organism wich one or more vectors comprising an expression cassette comprising a DNA sequence encoding a heterologous protein selected from the group consisting of hepatitis C virus (HCV) $E2_{715}$ envelope glycoprotein and human c-fos-induced growth factor (FIGF);
wherein said heterologous protein, when expressed, is localized in the ER and/or other secretory compartments.

26. A method according to claim 25, wherein said protein that catalyzes disulphide bond formation is protein disulphide isomerase (PDI).

27. A method according to claim 25, wherein said protein that catalyzes disulphide bond formation is TRX, and wherein said heterologous protein when expressed, does not form fusion protein(s) with said TRX.

28. A method according to any one of claims 25 to 24, wherein said host organism is a yeast.

* * * * *